(12) United States Patent
Newbold et al.

(10) Patent No.: US 9,265,756 B2
(45) Date of Patent: Feb. 23, 2016

(54) CRYSTALLINE FORMS OF GRAPIPRANT

(71) Applicant: Aratana Therapeutics Inc., Kansas City, KS (US)

(72) Inventors: Tamara Newbold, Martinsville, NJ (US); Melissa Smith, Germantown, WI (US); Christopher K. Seekamp, Germantown, WI (US); Robert Wenslow, Princeton, NJ (US); Xia Lu, Suzhou (CN)

(73) Assignee: Aratana Therapeutics, Inc., Kansas City, KS (US)

( * ) Notice: Subject to any disclaimer, the term of this patent is extended or adjusted under 35 U.S.C. 154(b) by 0 days.

(21) Appl. No.: 14/639,916

(22) Filed: Mar. 5, 2015

(65) Prior Publication Data

US 2015/0250774 A1    Sep. 10, 2015

Related U.S. Application Data

(60) Provisional application No. 61/949,006, filed on Mar. 6, 2014, provisional application No. 61/996,961, filed on Jul. 30, 2014.

(51) Int. Cl.
*C07D 401/14* (2006.01)
*A61K 31/437* (2006.01)

(52) U.S. Cl.
CPC ................... *A61K 31/437* (2013.01)

(58) Field of Classification Search
CPC .......................... C07D 401/14; A61K 31/437
USPC ........................... 546/119; 514/303
See application file for complete search history.

(56) References Cited

U.S. PATENT DOCUMENTS

| 6,710,054 | B2 | 3/2004 | Nakao et al. |
| 7,141,580 | B2 | 11/2006 | Nakao et al. |
| 7,479,564 | B2 * | 1/2009 | Nakao et al. |
| 7,960,407 | B2 | 6/2011 | Haruta et al. |

FOREIGN PATENT DOCUMENTS

| WO | 02032900 A3 | 8/2002 |
| WO | 2012157288 A1 | 11/2012 |

OTHER PUBLICATIONS

Goodman & Gilman's The Pharmacological Basis of Therapeutics, Tenth Edition (2001), Appendix II, pp. 475-493, McGraw Hill Medical Publishing Division, USA.

* cited by examiner

*Primary Examiner* — Niloofar Rahmani
(74) *Attorney, Agent, or Firm* — Polsinelli PC; Patrick C. Woolley

(57) ABSTRACT

The present disclosure provides a crystalline form of grapiprant selected from the group consisting of Form X, Form X2, Form X3, Form F, Form K, Form L, Form M, and Form N. Also provided is a pharmaceutical composition, the composition comprising at least one crystalline form of grapiprant, and at least one pharmaceutically acceptable excipient, wherein the crystalline form of grapiprant is selected from the group consisting of Form X, Form X2, Form X3, Form F, Form K, Form L, Form M, and Form N. Other aspects of the disclosure provide a process for preparing a substantially pure crystalline Form A of grapiprant. The process comprises contacting grapiprant at ambient temperature with a solvent comprising dichloromethane and acetone to form a saturated or a near saturated solution. Crystals of the substantially pure crystalline Form A of grapiprant are formed.

8 Claims, 17 Drawing Sheets

CRYSTALLINE FORMS OF GRAPIPRANT

CROSS-REFERENCE

This application claims the benefit under 35 U.S.C. §119(e) of U.S. Provisional Application Ser. No. 61/949,006, filed Mar. 6, 2014, and entitled "Crystalline Forms of Grapiprant," and of U.S. Provisional Application Ser. No. 61/996,961, filed Jul. 30, 2014, and entitled "Crystalline Forms of Grapiprant," both of which are incorporated by reference in their entireties.

TECHNICAL FIELD

The present disclosure generally relates to polymorphs of grapiprant and processes for their preparation.

BACKGROUND

Solids exist in either amorphous or crystalline forms. In the case of crystalline forms, molecules are positioned in three-dimensional lattice sites. When a compound recrystallizes from a solution or slurry, it may crystallize with different spatial lattice arrangements, and the different crystalline forms are sometimes referred to as "polymorphs." The different crystalline forms of a given substance may differ from each other with respect to one or more chemical properties (e.g., dissolution rate, solubility), biological properties (e.g., bioavailability, pharmacokinetics), and/or physical properties (e.g., mechanical strength, compaction behavior, flow properties, particle size, shape, melting point, degree of hydration or solvation, caking tendency, compatibility with excipients). The variation in properties among different crystalline forms usually means that one crystalline form may be more useful compared to other forms. For example, Form A, Form D, and Form J of grapiprant are known to exhibit different physical properties from one another.

Because grapiprant exhibits several advantageous therapeutic properties, improved forms of the compound are desired, particularly with regard to enhanced solubility, bioavailability, ease of synthesis, ability to be readily formulated, and/or physical stability. Thus, there is a need for improved crystalline forms of grapiprant and methods for preparing the different forms.

SUMMARY

Briefly, therefore, one aspect of the present disclosure encompasses a crystalline form of grapiprant selected from the group consisting of Form X, Form X2, Form X3, Form F, Form K, Form L, Form M, and Form N. The crystalline form is selected from the following group:

i. Form X, which exhibits an X-ray powder diffraction pattern having characteristic peaks expressed in degrees 2-theta at about 6.5, about 10.1, about 14.9, about 15.3, about 19.7, about 20.3, about 21.3, about 22.7, about 23.1, and about 27.3;

ii. Form X, which exhibits a differential scanning calorimetry profile having endotherm/exotherm events at about 33-80° C. and at about 110-140° C.;

iii. Form X, which exhibits a thermogravimetric analysis showing a loss of mass of 12-13% when heated from about 24° C. to about 150° C.;

iv. Form X2, which exhibits an X-ray powder diffraction pattern having characteristic peaks expressed in degrees 2-theta at about 10.2, about 14.9, about 16.8, about 18.3, about 21.8, about 22.7, about 23.9, about 24.3 about 25.9, and about 26.4;

v. Form X2, which exhibits a differential scanning calorimetry profile having endotherm/exotherm events at about 25-130° C., at about 130-150° C., and at about 150-190° C.;

vi. Form X2, which exhibits a thermogravimetric analysis showing a loss of mass of 14-15% when heated from about 25° to about 150° C.;

vii. Form X3, which exhibits an X-ray powder diffraction pattern having characteristic peaks expressed in degrees 2-theta at about 13.6, about 21.0, about 24.5, and about 25.3;

viii. Form X3, which exhibits a differential scanning calorimetry profile having endotherm/exotherm events at about 75-115° C., at about 135-150° C., and at about 150-170° C.;

ix. Form X3, which exhibits a thermogravimetric analysis showing a loss of mass of 10-11% when heated from about 25° to about 135° C.;

x. Form F, which exhibits an X-ray powder diffraction pattern having characteristic peaks expressed in degrees 2-theta at about 9.9, about 14.8, about 15.5, about 18.0, about 19.9, about 20.4, about 21.8, about 23.5, and about 27.7;

xi. Form F, which exhibits a differential scanning calorimetry profile having endotherm/exotherm events at about 122° C. and at about 143° C.;

xii. Form F, which exhibits a thermogravimetric analysis showing a loss of mass of about 20.5% when heated from about 25° to about 135° C.;

xiii. Form K, which exhibits an X-ray powder diffraction pattern having characteristic peaks expressed in degrees 2-theta at about 11.3, about 15.9, about 16.6, about 18.2, about 19.0, about 21.7, about 21.9, about 25.7, and about 29.0;

xiv. Form K, which exhibits a differential scanning calorimetry profile having endotherm/exotherm events at about 48° C., about 95° C., and at about 155° C.;

xv. Form K, which exhibits a thermogravimetric analysis showing a loss of mass of about 8.7% when heated from about 25° to about 135° C.;

xvi. Form L, which exhibits an X-ray powder diffraction pattern having characteristic peaks expressed in degrees 2-theta at about 6.8, about 11.1, about 13.8, about 16.7, about 20.7, about 23.2, about 25.0, about 26.0, and about 26.3;

xvii. Form L, which exhibits a differential scanning calorimetry profile having endotherm/exotherm events at about 106° C.;

xviii. Form L, which exhibits a thermogravimetric analysis showing a loss of mass of about 12.9% when heated from about 25° to about 135° C.;

xix. Form M, which exhibits an X-ray powder diffraction pattern having characteristic peaks expressed in degrees 2-theta at about 6.2, about 6.5, about 13.0, about 18.9, about 19.5, about 27.4, about 37.9, about 38.0, and about 39.7;

xx. Form M, which exhibits a differential scanning calorimetry profile having endotherm/exotherm events at about 77° C., at about 99° C., and at about 138° C.;

xxi. Form M, which exhibits a thermogravimetric analysis showing a loss of mass of about 13.6% when heated from about 25° to about 135° C.;

xxii. Form N, which exhibits an X-ray powder diffraction pattern having characteristic peaks expressed in degrees 2-theta at about 6.5, about 9.9, about 14.2, about 14.8, about 15.4, about 17.7, about 19.7, about 20.3, and about 23.4;

xxiii. Form N, which exhibits a differential scanning calorimetry profile having endotherm/exotherm events at about 121° C. and at about 157° C.; and xxiv. Form N, which exhibits a thermogravimetric analysis showing a loss of mass of about 11% when heated from about 25° to about 135° C.

Another aspect of the disclosure provides a pharmaceutical composition, the composition comprising at least one crystalline form of grapiprant, and at least one pharmaceutically acceptable excipient, wherein the crystalline form of grapiprant is selected from the group consisting of Form X, Form X2, Form X3, Form F, Form K, Form L, Form M, and Form N. The crystalline form may be selected from the group described above.

Other aspects of the disclosure provide a process for preparing a substantially pure crystalline Form A of grapiprant. The process comprises contacting grapiprant at ambient temperature with a solvent comprising dichloromethane and acetone to form a saturated or a near saturated solution. Crystals of the substantially pure crystalline Form A of grapiprant are formed, wherein the crystalline Form A exhibits an X-ray powder diffraction pattern having characteristic peaks expressed in degrees 2-theta at about 9.9, about 13.5, about 14.3, about 16.1, about 17.7, about 21.8, about 24.14, and about 25.8; a differential scanning calorimetry profile having showed an endotherm/exotherm at about 155-170° C.; and a thermogravimetric analysis showing a loss of mass of 0.5-0.6% when heated from about 30° to about 150° C. In some embodiments, the solvent may comprise a volume-to-volume ratio from 1:1 to 1:3 of dichloromethane/acetone. In other embodiments, the solvent may comprises 0 wt. % to 0.5 wt. % water.

Still other aspects of the disclosure provide a process for preparing a substantially pure crystalline Form X of grapiprant. The process comprises contacting grapiprant at 35° C. with a solvent comprising dichloromethane/acetone in a 1:0.5 to 1:5 volume-to-volume ratio to form a suspension.

Other features and iterations of the disclosure are described in more detail below.

DETAILED DESCRIPTION

Figure 1:
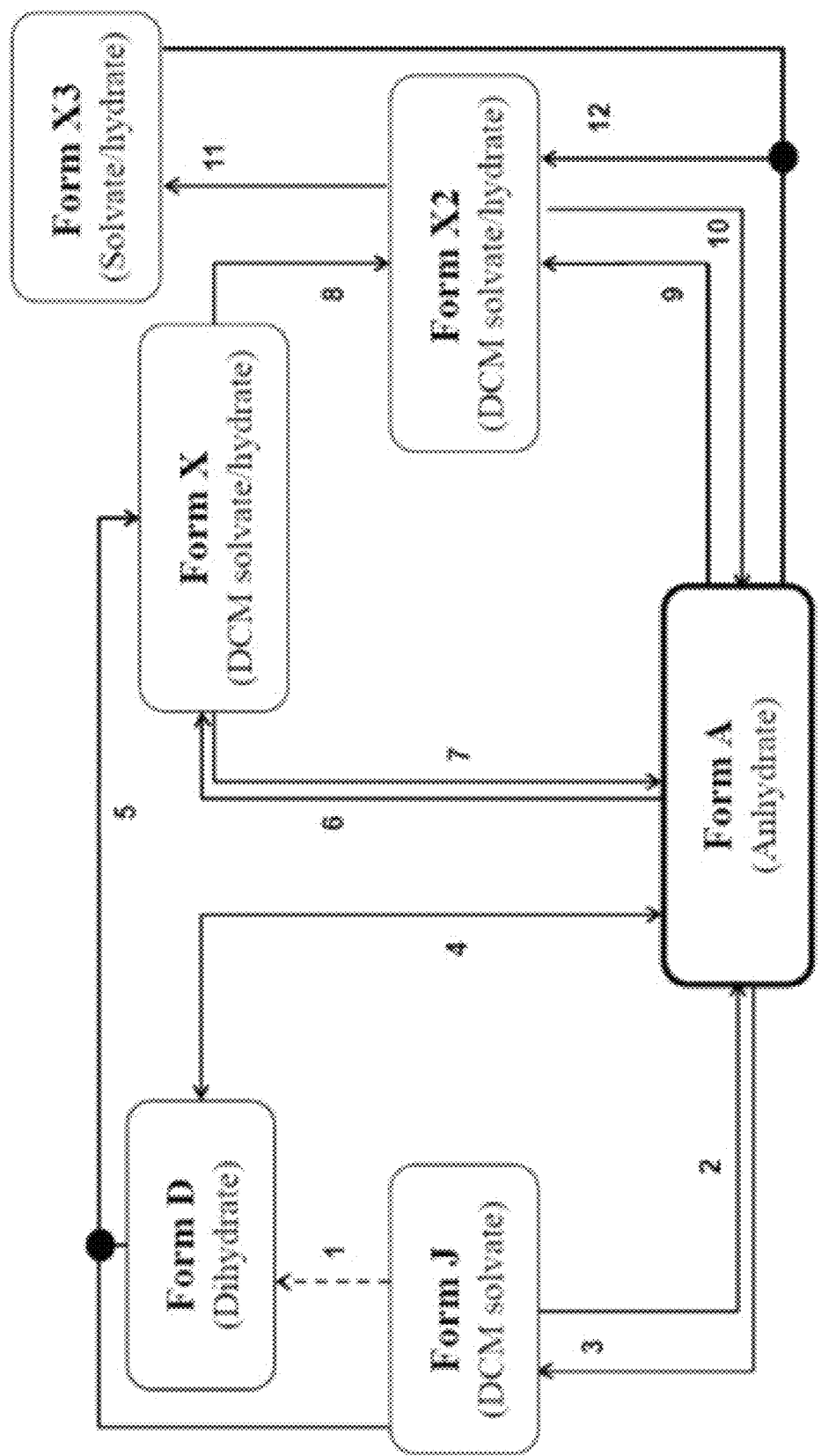
FIG. 1 depicts a process flowchart for converting the crystalline Forms A, D, J, X, X2, and X3 of grapiprant.

Grapiprant is a prostaglandin E2 subtype 4($EP_4$) receptor antagonist. Grapiprant has a CAS registry number of 415903-37-6 and is also referred to variously as CJ-023,423, RQ-7, RQ-00000007, MR10A7, AAT-007, N-{2-[4-(2-ethyl-4,6-dimethyl-1H-imidazo[4,5-c]pyridin-1-yl)phenyl]ethyl}-N'-[(4-methylphenyl) sulfonyl]urea, N-[[[2-[4-(2-ethyl-4,6-dimethyl-1H-imidazo[4,5-c]pyridin-1-yl)phenyl]ethyl]amino]carbonyl]-4-methyl-benenesulfonamide, or 2-ethyl-4,6-dimethyl-3-(4(2-(((((4-methylphenyl)sulfonyl)amino)carbonyl)amino)ethyl)phenyl)-3H-imidazo[4,5-c]pyridine. The chemical structure and synthesis of grapiprant are described in WO 2002/032900 and U.S. Pat. Nos. 6,710,054, 7,141,580, and 7,479,564, the disclosures of which are all incorporated by reference in their entireties. Grapiprant has the following chemical structure:

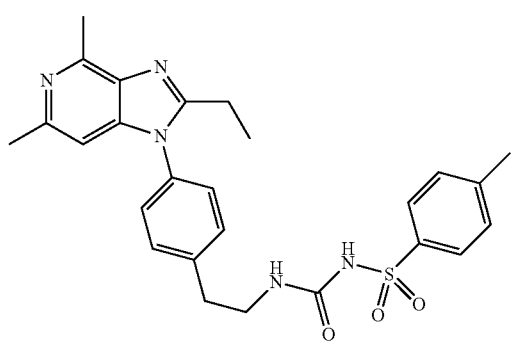

Without wishing to be bound by theory, prostaglandin E2 (PGE2) is a potent modulator involved in the pathogenesis of a variety of diseases such as inflammation, pain, arthritis, and cancer. PGE2 binds to at least four subtypes of PGE receptor, designated $EP_1$, $EP_2$, $EP_3$, and $EP_4$. Molecular pharmacology studies have revealed that all subtypes are 7-transmembrane spanning receptors that belong to the G-protein coupled receptor super family. $EP_1$ activation stimulates the release of intracellular calcium; $EP_2$ and $EP_4$ stimulation both activate adenylate cyclase but differ in their response to certain ligands; and $EP_3$ stimulation inhibits adenylate cyclase via inhibitory G-proteins.

In vivo, grapiprant inhibits [$^3$H]PGE binding to both human and rat $EP_4$ receptors with a $K_i$ of 13±4 and 20±1 nM, respectively. Grapiprant is highly selective for the $EP_4$ receptor over other human prostanoid receptor subtypes and inhibits $PGE_2$-evoked elevation in intracellular cAMP at the human and rat $EP_4$ receptors with $pA_2$ of 8.3±0.03 and 8.2±0.2 nM, respectively. Oral administration of grapiprant significantly reduces thermal hyperalgesia induced by intraplantar injection of $PGE_2$ ($ED_{50}$=12.8 mg/kg). Grapiprant is effective in models of acute and chronic inflammatory pain. Grapiprant significantly reduces mechanical hyperalgesia induced by carrageenan model and reverses complete Freund's adjuvant-induced chronic inflammatory pain response. Taken together, grapiprant is a potent and selective antagonist of both human and rat $EP_4$ receptors, produces antihyperalgesic effects in animal models of inflammatory pain.

It has been discovered that grapiprant may exist as any of several polymorphs. The polymorphs differ from each other with respect to their physical properties, spectral data, stability, and methods of preparation. Some crystalline forms have already been described, for example Form A, Form B, Form C, Form D, and Form G as described in U.S. Pat. No. 7,960,407, and ethyl acetate solvate Form I and Form II as described in WO 2012/157288, the disclosures of which are incorporated herein by reference in their entireties. Three new crystalline forms of grapiprant are described herein, and are hereinafter referred to, respectively, as From X, Form X2, Form X3, Form F, From K, Form L, Form M, and Form N. Also provided are processes for producing the different polymorphs of grapiprant, including Form A, From D, and From J.

(I) Crystalline Forms of Grapiprant

In one embodiment, grapiprant may exist as anhydrous Form A. Crystalline Form A exhibits an X-ray powder diffraction pattern comprising characteristic peaks expressed in degrees 2-theta as diagrammed in FIG. 2. In particular, Form A exhibits diffraction peaks at 5.326, 9.978, 12.599, 13.542, 13.803, 14.263, 16.121, 17.665, 18.053, 18.389, 19.126, 19.603, 20.314, 21.781, 22.949, 23.178, 23.663, 24.136, 25.803, 26.792, 27.160, 27.703, 28.125, 28.466, 29.326, 30.813, 31.699, 32.501, 33.219, 35.217, 36.285, 37.180, 38.079, and 39.141 degrees 2-theta. More specifically, Form A has predominant peaks at about 9.9, about 13.5, about 14.3, about 16.1, about 17.7, about 21.8, about 24.14, and about 25.8 degrees 2-theta (±0.15 degrees 2-theta). Form A exhibits a differential scanning calorimetry profile having an endotherm/exotherm at about 155-170° C. Form A also exhibits a thermogravimetric analysis showing a loss of mass of 0.5-0.6% when heated from about 30° to about 150° C.

In another embodiment, grapiprant may exist as dehydrate Form D. Crystalline Form D exhibits an X-ray powder diffraction pattern comprising characteristic peaks expressed in degrees 2-theta as diagrammed in FIG. 2. In particular, Form D exhibits diffraction peaks at 7.179, 7.511, 9.642, 12.493, 12.598, 13.411, 14.318, 14.978, 15.402, 15.694, 16.053, 17.680, 18.202, 19.223, 19.746, 20.570, 20.888, 21.327, 21.792, 22.313, 22.766, 23.284, 23.284, 23.676, 24.450, 24.755, 25.902, 27.142, 28.159, 30.224, 30.904, 32.374, 32.725, 34.237, 34.237, and 36.142 degrees 2-theta. More specifically, Form D has predominant peaks at about 9.6, about 12.5, about 15.0, about 15.4, about 22.7, and about 27.1 degrees 2-theta (±0.15 degrees 2-theta). Form D exhibits a differential scanning calorimetry profile having endotherm/exotherm events at about 25-125° C., at about 125-155° C., and at about 155-175° C. Form D also exhibits a thermogravimetric analysis showing a loss of mass of 6-7% when heated from about 24° to about 69° C.

In still another embodiment, grapiprant may exist as dichloromethane (DCM) solvate Form J. Crystalline Form J exhibits an X-ray powder diffraction pattern comprising characteristic peaks expressed in degrees 2-theta as diagrammed in FIG. 2. In particular, Form J exhibits diffraction peaks at 6.601, 10.158, 10.847, 11.432, 13.119, 14.281, 15.039, 15.470, 16.287, 17.810, 19.661, 20.479, 20.864, 21.395, 22.098, 22.857, 23.295, 24.767, 26.292, 27.343, 28.280, and 36.158 degrees 2-theta. More specifically, Form J has predominant peaks at about 6.6, about 13.1, about 15.5, about 19.7, and about 22.9 degrees 2-theta (±0.15 degrees 2-theta). Form J exhibits a differential scanning calorimetry profile having endotherm/exotherm events at about 25-105° C., at about 105-140° C., and at about 140-190° C. Form J also exhibits a thermogravimetric analysis showing a loss of mass of 10-11% when heated from about 28° to about 150° C. Form J may be a plate crystal.

In yet another embodiment, grapiprant may exist as DCM solvate/hydrate Form X. Crystalline Form X exhibits an X-ray powder diffraction pattern comprising characteristic peaks expressed in degrees 2-theta as diagrammed in FIG. 2. In particular, Form X exhibits diffraction peaks at 6.472, 10.062, 10.700, 11.282, 11.892, 12.097, 12.982, 13.285, 14.181, 14.926, 15.335, 16.164, 17.108, 17.730, 18.615, 19.577, 19.711, 20.315, 20.769, 21.313, 21.941, 22.712, 22.880, 23.142, 23.934, 24.359, 24.785, 26.121, 26.662, 27.261, 27.998, 28.622, 30.176, 31.793, 34.211, 35.970, and 37.491 degrees 2-theta. More specifically, Form X has predominant peaks at about 6.5, about 10.1, about 14.9, about 15.3, about 19.7, about 20.3, about 21.3, about 22.7, about 23.1, and about 27.3 degrees 2-theta (±0.15 degrees 2-theta). Form X exhibits a differential scanning calorimetry profile having endotherm/exotherm events at about 33-80° C. and at about 110-140° C. Form X also exhibits a thermogravimetric analysis showing a loss of mass of 12-13% when heated from about 24° to about 150° C.

In a further embodiment, grapiprant may exist as DCM solvate/hydrate Form X2. Crystalline Form X2 exhibits an X-ray powder diffraction pattern comprising characteristic peaks expressed in degrees 2-theta as diagrammed in FIG. 2. In particular, Form X2 exhibits diffraction peaks at 10.227, 12.020, 12.855, 13.221, 13.703, 14.919, 15.667, 16.234, 16.809, 17.170, 18.283, 18.791, 19.259, 19.815, 20.587, 21.227, 21.489, 21.812, 22.659, 23.445, 23.884, 24.338, 24.743, 25.131, 25.883, 26.391, 26.946, 27.629, 28.621, 29.995, 30.964, 31.757, 32.607, 33.716, 34.920, and 35.788 degrees 2-theta. More specifically, Form X2 has predominant peaks at about 10.2, about 14.9, about 16.8, about 18.3, about 21.8, about 22.7, about 23.9, about 24.3 about 25.9, and about 26.4 degrees 2-theta (±0.15 degrees 2-theta). Form X2 exhibits a differential scanning calorimetry profile having endotherm/exotherm events at about 25-130° C., at about 130-150° C., and at about 150-190° C. Form X2 also exhibits a thermogravimetric analysis showing a loss of mass of 14-15% when heated from about 25° to about 150° C.

In a still further embodiment, grapiprant may exist as solvate/hydrate Form X3. Crystalline Form X3 exhibits an X-ray powder diffraction pattern comprising characteristic peaks expressed in degrees 2-theta as diagrammed in FIG. 2. In particular, Form X3 exhibits diffraction peaks at 8.498, 10.042, 12.468, 13.609, 14.303, 14.923, 16.086, 16.773, 18.086, 19.231, 20.463, 21.010, 22.995, 24.477, 25.257, 26.206, 27.448, 28.739, and 33.619 degrees 2-theta. More specifically, Form X3 has predominant peaks at about 13.6, about 21.0, about 24.5, and about 25.3 degrees 2-theta (±0.15 degrees 2-theta). Form X3 exhibits a differential scanning calorimetry profile having endotherm/exotherm events at about 75-115° C., at about 135-150° C., and at about 150-170° C. Form X3 also exhibits a thermogravimetric analysis showing a loss of mass of 10-11% when heated from about 25° to about 135° C.

In some embodiments, grapiprant may exist as Form F. Crystalline Form F exhibits an X-ray powder diffraction pattern comprising characteristic peaks expressed in degrees 2-theta as diagrammed in FIG. 13. In particular, Form F exhibits diffraction peaks at 6.564, 8.047, 9.888, 11.430, 11.931, 13.152, 14.483, 14.759, 15.498, 16.129, 16.829, 17.669, 18.003, 18.288, 18.674, 19.111, 19.570, 19.924, 20.409, 21.835, 22.974, 23.485, 23.970, 24.564, 25.002, 26.284, 27.668, 28.158, and 34.174 (peaks listed with relative peak intensity >10%) degrees 2-theta. More specifically, Form F has predominant peaks at about 9.9, about 14.8, about 15.5, about 18.0, about 19.9, about 20.4, about 21.8, about 23.5, and about 27.7 degrees 2-theta (±0.15 degrees 2-theta). Form F exhibits a differential scanning calorimetry profile having endotherm/exotherm events at about 122° C. and at about 143° C. Form F also exhibits a thermogravimetric analysis showing a loss of mass of about 20.5% when heated from about 25° to about 135° C.

In some embodiments, grapiprant may exist as Form K. Crystalline Form K exhibits an X-ray powder diffraction pattern comprising characteristic peaks expressed in degrees 2-theta as diagrammed in FIG. 15. In particular, Form K exhibits diffraction peaks at 6.914, 9.683, 11.304, 12.380, 13.986, 14.391, 15.133, 15.942, 16.559, 16.870, 17.446, 17.771, 18.189, 19.044, 20.183, 21.714, 21.862, 22.498, 23.309, 24.054, 24.669, 25.083, 26.834, 27.836, 28.964, 31.968, 33.366, and 33.739 (peaks listed with relative peak intensity >10%) degrees 2-theta. More specifically, Form K has predominant peaks at about 11.3, about 15.9, about 16.6, about 18.2, about 19.0, about 21.7, about 21.9, about 25.7, and about 29.0 degrees 2-theta (±0.15 degrees 2-theta). Form K exhibits a differential scanning calorimetry profile having endotherm/exotherm events at about 48° C., about 95° C., and at about 155° C. Form K also exhibits a thermogravimetric analysis showing a loss of mass of about 8.7% when heated from about 25° to about 135° C.

In some embodiments, grapiprant may exist as Form L. Crystalline Form L exhibits an X-ray powder diffraction pattern comprising characteristic peaks expressed in degrees 2-theta as diagrammed in FIG. 17. In particular, Form L exhibits diffraction peaks at 6.836, 11.066, 13.755, 16.720, 17.636, 20.315, 20.726, 21.305, 21.970, 23.216, 24.491, 24.969, 26.022, 26.282, and 36.864 (peaks listed with relative peak intensity >1%) degrees 2-theta. More specifically, Form L has predominant peaks at about 6.8, about 11.1, about 13.8, about 16.7, about 20.7, about 23.2, about 25.0, about 26.0, and about 26.3 degrees 2-theta (±0.15 degrees 2-theta). Form L exhibits a differential scanning calorimetry profile having endotherm/exotherm events at about 106° C. Form L also exhibits a thermogravimetric analysis showing a loss of mass of about 12.9% when heated from about 25° to about 135° C.

In some embodiments, grapiprant may exist as Form M. Crystalline Form M exhibits an X-ray powder diffraction pattern comprising characteristic peaks expressed in degrees 2-theta as diagrammed in FIG. 19. In particular, Form M exhibits diffraction peaks at 6.162, 6.458, 10.561, 12.981, 14.974, 18.874, 19.538, 21.380, 25.101, 26.176, 27.382, 36.386, 37.883, 37.994, 39.714, and 39.816 (peaks listed with relative peak intensity >1%) degrees 2-theta. More specifically, Form M has predominant peaks at about 6.2, about 6.5, about 13.0, about 18.9, about 19.5, about 27.4, about 37.9, about 38.0, and about 39.7 degrees 2-theta (±0.15 degrees 2-theta). Form M, exhibits a differential scanning calorimetry profile having endotherm/exotherm events at about 77° C., at about 99° C., and at about 138° C. Form M also exhibits a thermogravimetric analysis showing a loss of mass of about 13.6% when heated from about 25° to about 135° C.

In other embodiments, grapiprant may exist as Form N. Crystalline Form N exhibits an X-ray powder diffraction pattern comprising characteristic peaks expressed in degrees 2-theta as diagrammed in FIG. 21. In particular, Form N exhibits diffraction peaks at 6.357, 6.472, 9.943, 10.007, 10.760, 11.313, 12.016, 12.938, 14.182, 14.763, 15.353, 16.000, 17.737, 18.350, 19.067, 19.506, 19.737, 20.311, 20.590, 21.376, 21.688, 22.912, 23.368, 24.066, 24.476, 25.838, 27.165, and 27.508 (peaks listed with relative peak intensity >10%) degrees 2-theta. More specifically, Form N has predominant peaks at about 6.5, about 9.9, about 14.2, about 14.8, about 15.4, about 17.7, about 19.7, about 20.3, and about 23.4 degrees 2-theta (±0.15 degrees 2-theta). Form N exhibits a differential scanning calorimetry profile having endotherm/exotherm events at about 121° C. and at about 157° C. Form N also exhibits a thermogravimetric analysis showing a loss of mass of about 11% when heated from about 25° to about 135° C.

(II) Pharmaceutical Compositions

Another aspect of the invention provides for a pharmaceutical composition comprising at least one polymorph of grapiprant and at least one pharmaceutically acceptable excipient. In some embodiments, the pharmaceutical composition may comprise at least one crystalline form of grapiprant and at least one pharmaceutically acceptable excipient, wherein the crystalline form of grapiprant is selected from the group consisting of Form X, Form X2, Form X3, Form F, Form K, Form L, Form M, Form N, and combinations thereof. The different crystalline forms of grapiprant are detailed above in Section (I).

A variety of excipients commonly used in pharmaceutical formulations may be selected on the basis of several criteria such as, for example, the desired dosage form and the release profile properties of the dosage form. Non-limiting examples of suitable excipients include an agent selected from the group comprising a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder, which holds the pharmaceutical composition together until administration. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, peptides, and combinations thereof.

In another embodiment, the excipient may be a filler, which adds bulk to the pharmaceutical composition for easier handling and more accurate dosing. Suitable fillers include carbohydrates, inorganic compounds, and polyvinylpyrrolidone. By way of non-limiting example, the filler may be calcium sulfate, e.g. both di- and tri-basic calcium sulfate; starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may be a non-effervescent disintegrant, which allows the pharmaceutical composition to more easily dissolve after administration without evolving gas. Suitable examples of non-effervescent disintegrants include starches (such as corn starch, potato starch, and the like), pregelatinized and modified starches thereof, sweeteners, clays (such as bentonite), microcrystalline cellulose, alginates, sodium starch glycolate, and gums (such as agar, guar, locust bean, karaya, pecitin, and tragacanth).

In another embodiment, the excipient may be an effervescent disintegrant, which allows the pharmaceutical composition to more easily dissolve during administration while evolving gas. By way of non-limiting example, suitable effervescent disintegrants include sodium bicarbonate in combination with citric acid, and sodium bicarbonate in combination with tartaric acid.

The excipient may comprise a preservative, which increases the stability and storage lifetime of the pharmaceutical composition, particularly delaying unwanted degradation of the active ingredient. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent, which diminishes the relative concentrations of other components within the pharmaceutical composition. Diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may include flavoring agents. Flavoring agents may be selected from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments, the flavoring agents and/or flavor-masking agents can comprise a vanilla-comprising composition, such as, but not limited to ethyl vanillin, vanillin (vanillin-RHD), natural vanilla flavor (vanillin-Merck), nature-identical vanilla flavor (vanilla-TG-old), and suitable solvents (e.g., ethanol and/or water).

In other embodiments, the flavoring agents and/or flavor-masking agents can comprise one or more selected from chicken, bacon, beef, pork, liver, fish, honey, caramel, and banana.

In some embodiments, the pharmaceutical composition that may be formulated for oral administration can include one or more of the following flavoring agents and/or flavor-masking agents (e.g., sweetening agents): sucralose; a dispersion of licorice, licorice derivatives, and licorice extract (glycyrrhizic acid/monoammonium glycyrrhizinate); MagnaSweet®; a blend of sodium saccharin and neohesperidin dihydrochalcone (Optisweet™ SD), 97:3 (w/w) mixture of sucrose and maltodextrin (Di-Pac®), thaumatin 7% (sweetener) blended with an inactive maltodextrin (Thaumatin T200X), pure thaumatin (Talin-Pure), stevia extract rebaudioside A (steviol glycosides), neotame, and/or polyols (sugar alcohols), such as sorbitol, maltitol, isomalt, xylitol, and glycerin.

As used herein "MagnaSweet®" refers to a composition consisting essentially of one or more sweeteners selected from the group consisting of glycyrrhizic acid (GA), monoammonium glycyrrhizinate (MAG), rebaudioside A, and glycerin. In some embodiments, the MagnaSweet® consists essentially of glycyrrhizic acid (GA), monoammonium glycyrrhizinate (MAG), rebaudioside A, and glycerin. In other embodiments, the MagnaSweet® consists essentially of glycyrrhizic acid (GA), monoammonium glycyrrhizinate (MAG), and glycerin. In some embodiments, the MagnaSweet® comprises from about 0.5% to about 25% GA/MAG, from about 0% to about 15% rebaudioside A, and from about 75% to about 99.5% glycerin. In other embodiments, the MagnaSweet® comprises from about 1.5% to about 17% GA/MAG, from about 0% to about 7.5% rebaudioside A, and from about 83% to about 91% glycerin. In exemplary embodiments, the MagnaSweet® comprises about 1.5% GA/MAG, about 7.5% rebaudioside A, and about 91% glycerin. In other exemplary embodiments, the MagnaSweet® comprises about 9% GA/MAG and about 91% glycerin. In another exemplary embodiment, the MagnaSweet® comprises about 17% GA/MAG and about 83% glycerin.

In particular, some sugar-containing sweeteners, such as saccharose-containing materials, sucrose, glucose, fructose, and maltodextrin, may at least partially degrade the capromorelin within the composition. Accordingly, large concentrations of some sugar-containing sweeteners should be avoided.

In exemplary embodiments, the flavoring agents or masking agents can comprise at least one of thaumatin, sucralose, neotame, sodium saccharain, neohesperidin dihydrochalcone, rebaudioside A, steviol glycosilde, licorice, glycyrrhizic acid, monoammonium glycyrrihizinate, sucrose, glucose, fructose, maltodextrin, sorbitol, maltitol, isomalt, glycerol, and a vanilla-comprising composition.

The excipient may comprise a surfactant, which alters the solubility parameters of the other components within the pharmaceutical composition. In various embodiments, the surfactant may be a alkylaryl polyether alcohol, such as Triton™ X-100, Surfonic™ N-100 (nonoxaynol-10), or Witconol™ NP-100; or a poloxamer, such as Pluronic™, Synperonic™, or Kolliphor™. Other suitable examples of surfactants include, for example, 2-acrylamido-2-methylpropane sulfonic acid, alkyl polyglycoside, ammonium perfluorononanoate, benzalkonium chloride (BAC), benzethonium chloride (BZT), 5-bromo-5-nitro-1,3-dioxane, cetyl trimethylammonium bromide (CTAB, hexadecyltrimehtylammonium bromide, cetyl trimethylammonium chloride), cetylpridinium chloride (CPC), cyclohexyl-1-hexyl-maltopyranoside, decylmaltopyranoside, decyl polyglucose, dimethyldioctadecylammonium chloride, dioctadecyldim-ethylammmonium bromide (DODAB), dipalmitoylphos-phatidylcholine, lauryldimethylamine oxide, dodecylmalto-pyranoside, magnesium laureth sulfate polyethoxylated tallow amine (POEA), octenidine dihydrochloride, octylphe-noxypolyethoxyethanol (Igepal™ CA-630), octylthioglu-copyranoside (OTG), ox gall, sodium nonanoyloxybenzen-sulfonate, sorbitan monolaurate, surfactin, and thonozonium bromide. In exemplary embodiments, the surfactant may be a poloxamer or sodium lauryl sulfate.

In another embodiment, the excipient may be a lubricant, which allows easier removal of the pharmaceutical composition from molds during manufacture and may aid administration of the pharmaceutical composition. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer, which aids dispersion of the components of the pharmaceutical composition within the subject after administration. Suitable dispersants may include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent, which aids visualization and identification of the pharmaceutical composition. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Taste-masking materials include cellulose hydroxypropyl ethers (HPC); low-substituted cellulose hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In various embodiments, the excipient may include a pH modifier, which may alter the solubility profile and bioavailability parameters of components within the pharmaceutical composition. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semi-solids; or gels. Other suitable dosage forms include transdermal systems or patches. The transdermal system may be a matrix system, a reservoir system, or a system without rate-controlling membranes.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., prilling, spray drying, pan coating, melt granulation, granulation, wurster coating, tangential coating, top spraying, extruding, coacervation and the like.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's *The Pharmacological Basis of Therapeutics*, Tenth Edition (2001), Appendix II, pp. 475-493, and the Physicians' Desk Reference.

(III) Processes for Preparing Substantially Pure Polymorphs of Grapiprant

A further aspect of the present invention provides processes for producing substantially pure polymorphs of grapiprant. The phrase "substantially pure," as used herein, means that the polymorph has a purity of about 95% by weight, or more preferably about 97% by weight, as defined by X-ray powder diffraction. Stated another way, the polymorph has no more than about 5% by weight, or more preferably no more than about 3% by weight, of another polymorph of grapiprant. The different polymorphs of grapiprant are detailed above in Section (I).

In general, in some embodiments, the process for preparing a substantially pure crystalline Form A of grapiprant comprises contacting grapiprant at ambient temperature with a solvent comprising dichloromethane and acetone to form a saturated or a near saturated solution. Crystals of the substantially pure crystalline Form A of grapiprant are formed, wherein the crystalline Form A exhibits an X-ray powder diffraction pattern having characteristic peaks expressed in degrees 2-theta at about 9.9, about 13.5, about 14.3, about 16.1, about 17.7, about 21.8, about 24.14, and about 25.8; a differential scanning calorimetry profile having showed an endotherm/exotherm at about 155-170° C.; and a thermogravimetric analysis showing a loss of mass of 0.5-0.6% when heated from about 30° to about 150° C.

In other embodiments, the disclosure provides process for preparing a substantially pure crystalline Form X of grapiprant. The process comprises contacting grapiprant at 35° C. with a solvent comprising dichloromethane/acetone (1:1, v/v) to form a suspension. Crystals of the substantially pure crystalline Form X of grapiprant are formed, wherein the crystalline Form X, which exhibits an X-ray powder diffraction pattern having characteristic peaks expressed in degrees 2-theta at about 6.5, about 10.1, about 14.9, about 15.3, about 19.7, about 20.3, about 21.3, about 22.7, about 23.1, and about 27.3; a differential scanning calorimetry profile having endotherm/exotherm events at about 33-80° C. and at about 110-140° C.; and a thermogravimetric analysis showing a loss of mass of 12-13% when heated from about 24° C. to about 150° C. In exemplary embodiments, the process may further comprise converting Form X to Form A by slurry in dichloromethane/acetone with a volume-to-volume ratio of 1:1.

The solvent used in the process can and will vary depending upon the embodiment. In general, the solvent may be a protic solvent, an aprotic solvent, or combinations thereof. Suitable protic solvents include, but are not limited to, water, methyl alcohol, ethyl alcohol, isopropyl alcohol, n-propyl alcohol, isobutyl alcohol, n-butyl alcohol, s-butyl alcohol, t-butyl alcohol, formic acid, acetic acid, and combinations thereof. Non-limiting examples of suitable aprotic solvents include acetone, acetonitrile, dichloromethane, tetrahydrofuran, and combinations thereof. The grapiprant that is contacted with the solvent may be in a solid form (e.g., a powder) or a liquid form (e.g., in a solution comprising a co-solvent, or a concentrated oil/gel/gum). The weight ratio of solvent to grapiprant may range from about 2 to about 10, or more preferably from about 4 to about 7.

The temperature of the process can and will vary depending upon the embodiment. The temperature of step (a) may range from about 4° C. to about the boiling temperature of the solvent. In one embodiment, step (a) may be conducted at a temperature that ranges from about 4° C. to about 25° C. In another embodiment, step (a) may be conducted at a temperature that ranges from about 25° C. to about 60° C. In still another embodiment, step (a) may be conducted at a temperature that ranges from about 60° C. to about 100° C. In a further embodiment, step (a) may be conducted at a temperature that ranges from about 100° C. to about 150° C.

The temperature of step (b) may also range from about −10° C. to about 150° C. In one embodiment, step (b) may be conducted at temperature that ranges from about −10° C. to about 20° C. In another embodiment, step (b) may be conducted at a temperature that ranges from about 20° C. to about 50° C. In an alternate embodiment, step (b) may be conducted at a temperature that ranges from about 50° C. to about 100° C. In another alternate embodiment, step (b) may be conducted at a temperature that ranges from about 100° C. to about 150° C.

The crystals of substantially pure grapiprant may be formed by a variety of methods, as detailed in the Examples. In some embodiments, the crystals may be formed by "slow evaporation." For this, the solvent is typically slowly evaporated such that crystals form slowly. The rate of evaporation may be slowed by placing the saturated or near saturated solution in a flask with a narrow opening, covering the opening with paper or foil comprising a few small holes, or sealing the opening with a cap into which a needle has been inserted. Evaporation of the solvent may be conducted in the presence of air or in an inert environment (i.e., under nitrogen or argon). The solvent may be evaporated at atmospheric pressure or at a pressure that is less than atmospheric pressure.

In other embodiments, the crystals may be formed by "hot crystallization" or "hot recrystallization." For this, step (a) of the process is conducted at an elevated temperature. Typically, the temperature of this step is at or near the boiling point of the solvent. The solvent may be removed at an elevated temperature, wherein crystals precipitate out of the hot solution. Alternatively, the hot solution may be allowed to cool, wherein crystals precipitate out of the cool solution.

The process generally further comprises collecting the solids of substantially pure grapiprant. The solids may be collected by filtration, centrifugation, or other techniques well known in the art. The process may further comprise drying the solids of substantially pure grapiprant. The solids may be dried under a vacuum either at room temperature or at an elevated temperature.

In some embodiments, crystalline Form X of grapiprant base may be prepared by crystallization of grapiprant in a solvent comprising dichloromethane and acetone.

In some embodiments, crystalline Form X2 of grapiprant base may be prepared by crystallization of grapiprant in a solvent comprising from about 1:1 to about 1.4 dichloromethane/acetone with about 0 wt. % to about 0.5 wt. % water. In exemplary embodiments, the crystallization may use about 0.3 wt. % water.

In some embodiments, crystalline Form X3 of grapiprant base may be prepared by drying Form X2 of grapiprant.

As various changes could be made in the above compounds and processes without departing from the scope of the invention, it is intended that all matter contained in the above description and in the examples given below, shall be interpreted as illustrative and not in a limiting sense.

DEFINITIONS

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (0), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of oxygen protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present disclosure or the embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the disclosure in detail, it will be apparent that modifications and variations are possible without departing from the scope of the disclosure defined in the appended claims.

EXAMPLES

The following examples are included to demonstrate certain embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

General Protocols

Slow Evaporation.

To form crystals by slow evaporation, a saturated or near saturated solution was prepared by mixing grapiprant in the appropriate solvent or solvent system. A small vial of the saturated/near saturated solution was placed in a nitrogen-purged desiccator at room temperature. Following crystal growth, the crystals were filtered from the residual solvent, if necessary, using a fritted disc funnel or a Büchner funnel using a Whatman #1 filter paper.

Hot Crystallization.

To form crystals by hot crystallization, the appropriate solvent was heated to boiling or near boiling, and grapiprant was slowly added until the solution was saturated or near saturated. The solution was allowed to cool at room temperature. Following crystal growth, the crystals typically were filtered from the solvent using a fritted disc funnel. In some experiments, the filtrates were then allowed to slowly evaporate under nitrogen purge to encourage crystal growth. In some cases, the crystals were dried at elevated temperatures.

Slurry Experiments.

The stability of the crystalline forms was analyzed using slurry experiments. A portion of the solvent of interest was saturated with grapiprant in a small vial. Additional grapiprant was then added to the vial, and the resulting slurry was stirred using a magnetic stir bar.

X-Ray Powder Diffraction.

The X-ray powder diffraction (XRPD) pattern was determined using an X-ray diffractometer. The instrument was equipped with a long fine focus X-ray tube (with a copper Kα radiation source operated at 45 kV/40 mA), and a diffracted beam monochromator mounted in front of a scintillation detector. The instrument parameters included a scan range of 3.0 to 40.0 degrees 2-theta, a step size of 0.02 degrees 2-theta, and a scan time of 12.7 seconds per step. The instrument was interfaced with a computer for data acquisition and analysis. Each sample was uniformly crushed with a spatula edge and placed on a quartz, zero-background holder.

Differential Scanning Calorimetry.

Differential scanning calorimetry (DSC) was performed using a differential scanning calorimeter. The instrument was calibrated using indium. Each sample was weighed into a hermetic aluminum sample pan and sealed with a pinhole lid. The samples were heated from 22° C. to the designated temperature at a rate of 5° C. per minute, unless otherwise indicated.

Thermogravimetric Analysis.

Thermogravimetric analysis (TGA) was performed with a thermogravimetric analyzer equipped with a quartz-lined evolved gas furnace for TGA Fourier transform infrared (FTIR) experiments. The FTIR spectrometer for the TGA-FTIR analyses was equipped with a TGA interface furnace, gas cell and a transfer line. Each sample was weighed into an aluminum sample pan and placed into the instrument. The samples were heated from room temperature to the designated temperature at a rate of 10° C. per minute, unless otherwise indicated, with a nitrogen flow of 50 mL per minute. For the TGA-FTIR experiments, the transfer line and TGA interface furnace were held at 150° C. A Gram-Schmidt plot/analysis was attained for each experiment, with individual spectra of evolved gases analyzed with 16 scans at a resolution of 8 $cm^{-1}$. A background (16 scans) was acquired prior to each experiment.

Water Vapor Sorption.

Data were collected with a water vapor sorption balance. A portion of the selected sample was weighed into a platinum sample pan and placed into the instrument. The sample was cycled from low (5%) relative humidity (RH) to high (95%) RH to low humidity (i.e., sorption and desorption events) at a constant temperature of 25° C., in 5% RH intervals. The sample was held at each interval until the equilibrium condition was met (i.e., 0.0005% for 3 min, with a maximum of 600 min).

Example 1

Exploration of crystalline polymorphs of grapiprant

Figure 11:
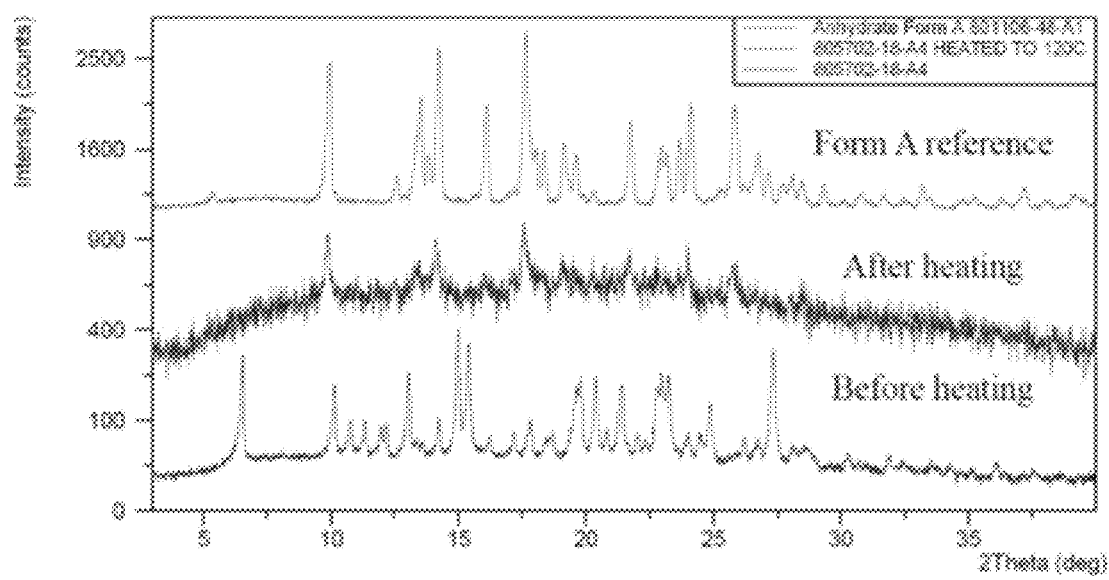
FIG. 11 shows the XRPD patterns demonstrating that Form J is converted into Form A after heating to 120° C.
Figure 12:
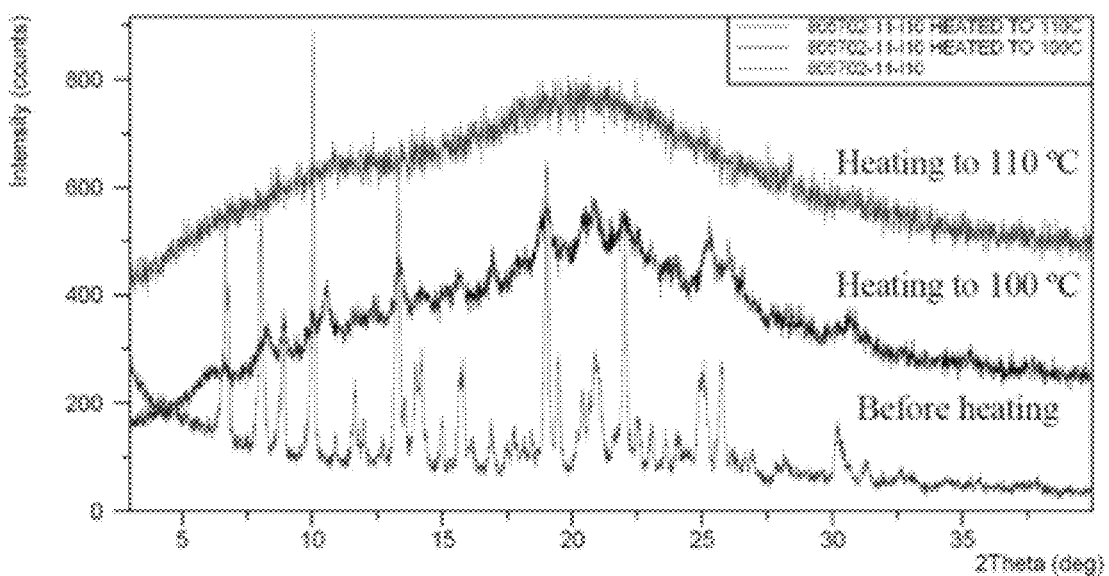
FIG. 12 shows the XRPD patterns demonstrating that Form X is converted into amorphous after heating to 110° C.

Form A may be recrystallized in THF/n-heptane via an anti-solvent addition, providing a HPLC purity of 98.9 A % with residual THF of 0.7 wt. %. Theoretical dichloromethane (DCM) wt. % for 1:1 DCM/grapiprant is 14.7%. Tables 1 and 2 below summarize these results. Form A of grapiprant is more stable than Form J (DCM solvate) in 1:1 DCM/acetone (v/v). Form J becomes Form A in DCM/acetone 1:2 or by heating to 120° C. (See FIG. 11.). Form A becomes Form J in DCM/heptanes 2:1. Form J becomes Form X if slurried in acetone or heptanes. Form X becomes amorphous when heated to 110° C. Reaction in THF consumed much higher amounts of p-toluenesulfonylisocyanate starting material than that required in dichloromethane.

Form X2 converts to Form A in DCM/acetone at a ratio of as low as 1:3 (v/v) with only 0.3 wt. % water in the product. Water is not typically added and may be residual in the acetone. Anti-solvent addition from 0:1 to 1:1 gives a mixture of Forms A and J, or just Form J, which can be converted into Form A in acetone or 1:1 to 1:2 DCM/acetone. The products meet the residual solvent specifications. Simultaneous addition at 1:2 or 1:3 DCM/acetone gives a mixture of Forms A and X2. Form X2 cannot be easily converted to Form X3. Residual solvent cannot be easily removed.

Overall, FIG. 1 summarizes the relationship of each polymorphic form with relationship to each other. Form J may be converted to Form D by drying in air (1). Form J may be converted to Form A by slurry in DCM/acetone (<1:2 v/v) at 25° C. (2). Form A may be converted to Form J by precipitation from DCM/n-heptane (2:1 v/v) (3). Forms A and D have an $a_w$ value of about 0.6 at room temperature (4). Form X may be converted from a slurry mixture of Form D and Form J in DCM/acetone or DCM/n-heptane (2:1 v/v) at room temperature (5). Form X may be converted to Form A by slurry in DCM/acetone (1:1 v/v) (6). Form A may be converted to Form X by slurry in DCM/acetone (≤1:3 v/v (7) or 1:2 v/v with 0.3 wt. % water (8)). Form X2 may be converted to Form A by slurry in DCM/acetone (1:3 v/v) with 0.3 wt. % water (9). Form A may be converted to Form X2 by slurry in acetone with 0.3 wt. % water (10). Form X2 may be converted to Form X3 by drying (11). Form X2 may also be generated by slurry of Forms A and X3 in DCM/acetone (1:3 v/v) with 0.3 wt. % water (12).

Further experimental details are found below in Tables 1-13. Examples 2-12 provide further details regarding the characterization of Forms A, D, J, X, X2, X3, F, K, L, M, and N, respectively.

TABLE 1

Solvent systems tested.

| Starting Material | Solvent System | | Results | |
|---|---|---|---|---|
| | Name | Ratio (v:v) | Final form by XRPD | Residual Solvents by GC (wt. %) |
| Crystallization product from DCM/n-heptane: Forms D & J | DCM/ acetone | 2:1<br>1:3<br>1:9 | Unidentified<br>Form A<br>Form A | —<br>—<br>— |
| | DCM/n-heptane | 2:1<br>1:3<br>1:9 | Unidentified<br>Form D<br>Form D | —<br>—<br>— |
| Crystallization product from DCM/acetone: Forms A & J | Acetone | — | Form A | 0.18% acetone + 0.18% DCM |
| | DCM/ acetone | 1:1 | Form J | 1.96% acetone + 20.32% DCM |

TABLE 2

Preliminary crystallization via anti-solvent addition in THF/n-heptane, using 8.4 g grapiprant Form A as the starting material.

| Staring | Anti-solvent addition | | | | Cooling | | Results | |
|---|---|---|---|---|---|---|---|---|
| Conc. (mg/mL) | Temp (° C.) | Time (h) | Anti-solvent | End THF (vol. %) | Time (h) | End Temp. (° C.) | HPLC Purity (A %) | Residual THF (wt. %) |
| 80 | 40 | 12 | 1:2 THF/n-heptane | 60 | 1 | 20 | 98.9 | 0.662 |

TABLE 3

Summary of new form preparation and characterization.

| Form by XRPD | Preparation Method | TGA Wt Loss (wt %) | GC Results (wt %) | KF (wt %) |
|---|---|---|---|---|
| D | Form A slurry in water | 6.72 | n.a | n.a |
| J | Precipitate in DCM/n-heptane (v:v = 2:1) | 13.76 | DCM 11.81 Acetone 0.67 (NMR data) | 0.19 |
| X | Form D and Form J slurry in DCM/Acetone (v:v = 2:1) | 9.47 | DCM 8.10 Acetone 0.39 (NMR data) | 1.36 |
| X2 | Form A (contain three new peaks) Slurry in DCM/Acetone/$H_2O$ (v:v:v = 33:66:1) | 19.2 | DCM 12.1 Acetone 7.2 | n.a |
| X3 | Form X2 drying at r.t. or 45° C. | 10.06 | DCM 8.8 Acetone 4.5 | 1.06 |

TABLE 4

Slurry conversion in acetone of the product from the anti-solvent crystallization in DCM/acetone.

| Sample No. | Slurry T (° C.) | Slurry Time (h) | Drying T (° C.) | Form by XRPD | Residual DCM (wt. %) | Residual Acetone (wt. %) | TGA (wt. %) |
|---|---|---|---|---|---|---|---|
| 1 | — | — | — | A + J | 4.660 | 0.430 | 6.24 |
| 2 | 23 | 16 | 50 | A | 0.057 | N/A | 0.62 |
| 3 | 45 | 22 | 50 | A | 0.054 | N/A | 0.38 |
| 4 | 45 | 22 | 50 | A | 0.050 | 0.158 | N/A |
| 5 | 45 | 39 | 50 | A | 0.003 | 0.243 | 0.44 |

TABLE 5

Crystallization via simultaneous addition at 1:2 and 1:3 DCM/acetone.

| | Seed bed preparation | | | Line A: API/Acetone solution (Line B: Acetone) | | | | | DCM/Acetone | |
|---|---|---|---|---|---|---|---|---|---|---|
| Sample No. | T (° C.) | Load (wt. %) | Conc. (mg/mL) | T (° C.) | Time (h) | Conc. (mg/mL) | Purity (A %) | Solvent | in the end (v:v) | Final T (° C.) |
| 6 | 35 | 25 | 58.5 | RT | 18 | 150 | 90.9 | DCM | 1/2 | 15 |
| | | | | | | (a) Product => Slurry in Acetone (RT, 36 hrs) | | | | |
| | | | | | | (b) Product => Slurry in 1:2 DCM/Acetone (RT, 36 hrs) | | | | |
| 7 | 35 | 25 | 55.6 | RT | 18 | 150 | 90.9 | DCM | 1/2 | 8 |
| | | | | | | (a) Product => Slurry in Acetone (RT, 18 hrs) | | | | |
| 8 | 35 | 25 | 63.4 | RT | 19 | 180 | 90.3 | DCM/Acetone 4:1 | 1/3 | 15 |

TABLE 6

Results from crystallization via simultaneous addition at 1:2 and 1:3 DCM/acetone.

| | | | | Results | | | |
|---|---|---|---|---|---|---|---|
| Sample No. | Crystal Type | Water content (wt %) | Purity (A %) | Residual Solvent wt % (GC) | | Yield* (by ML) | |
| | | | | DCM | Acetone | | |
| 6 | A + X2 | 0.51 | 99.8 | 0.183 | 0.178 | 20.3 | |
| 6a | A + X2 | — | n.a | pending | pending | n.a | |
| 6b | A + X2 | — | n.a | 0.145 | 0.126 | n.a | |
| 7 | A + X2 | 2.05 | 99.6 | 2.768 | 1.569 | 80.9 | |
| 7a | A + X2 | 1.16 | n.a | pending | pending | n.a | |
| 8 | A + X2 | pending | pending | pending | pending | pending | |

TABLE 7

Results from crystallization via slurry at room temperature.

| Solvent (v/v) | Final Form |
|---|---|
| DCM/THF, 2:3 | Form A |
| DCM/1,4-Dioxane, 2:3 | Form A |
| DCM/Ethanol, 2:3 | no solid available |
| DCM/Acetonitrile, 2:3 | Form A |
| DCM/Chloroform, 2:3 | Form F |
| DCM/Ethyl Acetate, 2:3 | Form A |
| DCM/Toluene, 2:3 | Form J + Form A |
| DCM/Heptane, 2:3 | Form J + Form A |
| DCM/Heptane, 1:4 | Form A |
| DCM/Heptane, 1:1 | Form J + Form A |
| DCM/Heptane, 4:1 | Form J + Form A |
| DCM/Acetone/Water, 1:1:1 | Form D |
| DCM/Acetone/THF, 1:1:2 | Form A + Form D |
| DCM/Acetone/Acetonitrile, 1:1:2 | Form A |
| DCM/Acetone/Ethyl Acetate, 1:1:2 | Form A |

TABLE 7-continued

Results from crystallization via slurry at room temperature.

| Solvent (v/v) | Final Form |
|---|---|
| Acetone/Chloroform, 1:1 | Form F |
| DCM/Acetone/Toluene, 1:1:2 | Form A |
| Acetone/THF, 1:2 | Form A |
| DCM/Acetone, 7:5 | Amorphous |
| Chloroform/Acetone, 5:1 | Form F |

TABLE 8

Results from crystallization via slurry at 50° C.

| Solvent (v/v) | Final Form |
|---|---|
| DCM/2-MeTHF, 1:4 | Form A |
| DCM/Isopropanol, 1:5 | Form A |
| DCM/Methyl ethyl ketone, 1:4 | Form A |
| DCM/Isopropyl acetate, 1:4 | Form A |
| DCM/Toluene, 1:5 | Form A |
| DCM/Acetone/Water, 1:2:1 | amorphous |
| DCM/Acetone/1,4-Dioxane, 1:2:1 | Form A |
| DCM/Acetone/Ethanol, 1:2:1 | no solid available |
| DCM/Acetone/Toluene, 1:2:2 | Form A |
| DCM/Acetone, 1:5 | Form A |
| DCM/Acetone, 1:1 | Form A |
| DCM/Acetone, 3:1 | Form J + Form A |
| Acetone/Heptane, 3:1 | Form A |
| Acetone/THF, 4:1 | Form A |

TABLE 9

Results from crystallization via cooling.

| Method | Solvent (v/v) | Concentration | Final Form |
|---|---|---|---|
| 0.1° C./min from 50° C. to 5° C. | DCM/Acetone, 1:3 | saturated | Form J + Form A |
| | DCM/Acetone, 1:1 | saturated | Form J + Form D |
| | DCM/Heptane, 3:1 | saturated | Form J |
| | DCM/Ethanol, 1:3 | saturated | N/A |
| | DCM/THF, 2:3 | saturated | Form A |
| | DCM/Isopropyl acetate, 1:4 | saturated | Form D |
| | DCM/Toluene, 2:3 | saturated | Form J + Form X |
| | DCM/Acetonitrile, 1:5 | saturated | Form J + Form X |
| | DCM/Methyl isobutyl ketone, 3:2 | saturated | Form J + Form X |
| | DCM/Isopropanol, 5:1 | saturated | N/A |
| | DCM/Acetone, 9:1 | 100 mg/mL | N/A |
| | DCM/Acetone, 7:1 | 50 mg/mL | Form J |
| | DCM/Acetone, 4:1 | 20 mg/mL | Form J + Form X |
| Quickly cooled from 50° C. to RT | DCM/Acetone, 1:1 | saturated | Form J |
| | DCM/Heptane, 3:1 | saturated | Form J |
| | DCM/Acetone, 3:1 | saturated | Form J |
| Quickly cooled from 50° C. to 5° C. | DCM/Ethanol, 1:2 | saturated | N/A |
| | DCM/THF, 2:3 | saturated | Form J |
| | DCM/Acetone, 2:1 | saturated | no solid available |

TABLE 10

Results from crystallization via liquid vapor diffusion.

| Solvent (v/v) | Anti-solvent | Final Form |
|---|---|---|
| DCM | Acetone | no solid available |
| DCM | Isopropanol | no solid available |
| DCM | Ethyl acetate | Form A |
| DCM | THF | no solid available |
| DCM | 1,4-Dioxane | no solid available |
| DCM | Acetonitrile | no solid available |
| DCM | Hexane | no solid available |

TABLE 10-continued

Results from crystallization via liquid vapor diffusion.

| Solvent (v/v) | Anti-solvent | Final Form |
|---|---|---|
| DCM | Toluene | no solid available |
| DCM/Acetone, 5:1 | Methyl ethyl ketone | Form A |
| DCM/Acetone, 3:1 | Ethanol | Form A |

TABLE 11

Results from crystallization via anti-solvent addition.

| Solvent | Anti-solvent | Final Form |
|---|---|---|
| DCM | Acetone | no solid available |
| DCM | Ethanol | Form L (after slurry at 5° C.) |
| DCM | Isopropyl Acetate | Form A |
| DCM | 2-MeTHF | no solid available |
| DCM | 1,4-Dioxane | no solid available |
| DCM | Acetonitrile | Form L (after slurry at 5° C.) |
| DCM | Hexane | Form J |
| DCM | Toluene | Form A |
| DCM | Methyl isobutyl ketone | Form A |
| DCM | Methyl ethyl ketone | no solid available |

TABLE 12

Results from crystallization via evaporation.

| Solvent (v/v) | Conc. (mg/mL) | Temperature | Final Form |
|---|---|---|---|
| DCM/Acetone, 3:1 | 10 | room temperature | amorphous |
| DCM/Acetone, 7:3 | 30 | room temperature | Form M |
| DCM/Acetone, 9:1 | 100 | room temperature | Form J |
| DCM/Methanol, 1:1 | 20 | room temperature | no solid available |
| DCM/THF, 5:1 | 20 | room temperature | no solid available |
| DCM/Methyl t-butyl ether, 3:1 | 20 | room temperature | Form J |
| DCM/Acetonitrile, 1:1 | 20 | room temperature | no solid available |
| DCM/Methyl ethyl ketone, 3:1 | 20 | room temperature | Form J |
| Acetone/Methanol, 1:3 | 20 | room temperature | no solid available |
| Acetone/Water, 1:1 | 20 | 50 | amorphous |
| DCM/Toluene, 4:1 | 20 | 50 | amorphous |
| DCM/Ethyl acetate, 4:1 | 20 | 50 | amorphous |
| DCM/Heptane, 5:1 | 20 | 35 | Form J |
| DCM/Isopropyl acetate, 5:1 | 20 | 35 | no solid available |
| DCM/Acetone, 1:2 | 10 | 5 | amorphous |
| DCM/Acetone, 2:1 | 10 | 5 | no solid available |
| DCM/Methanol, 2:1 | 10 | 5 | no solid available |
| DCM/Acetone, 9:1 | 50 | room temperature | Form J |

TABLE 13

Results from crystallization via evaporation.

| Solvent (v/v) | Polymer | Final Form |
|---|---|---|
| DCM/Acetone, 7:1 | Mixture I: | Form J |
| DCM/THF, 5:1 | polyvinyl pyrrolidone (PVP), | Form N |
| DCM/Methanol, 1:1 | polyvinyl alcohol (PVA), | amorphous |
| Acetone/Methanol, 1:5 | polyvinylchloride (PVC), polyvinyl acetate (PVAC), | no solid available |

TABLE 13-continued

Results from crystallization via evaporation.

| Solvent (v/v) | Polymer | Final Form |
|---|---|---|
| DCM/Acetone/Water, 1:1:0.5 | hypromellose (HPMC), methyl cellulose (MC) (mass ratio of 1:1:1:1:1:1) | amorphous |
| DCM/Acetonitrile, 5:1 DCM/Ethyl acetate, 4:1 DCM/Heptane, 9:1 Acetone/Water, 5:1 | Mixture II: polycaprolactone (PCL), polyethylene glycol (PEG), poly (methyl methacrylate) (PMMA), sodium alginate (SA), | Form K Form A Amorphous no solid available |
| DCM/Acetone/Water, 1:1:0.5 | hydroxyethyl cellulose (HEC) (mass ratio of 1:1:1:1:1). | Amorphous |

Example 2

Preparation and Characterization of Form a Crystals

Form A of grapiprant is an anhydrate, having less than 0.2% by weight of water. Form A crystals were prepared by (1) slurry of Form J (Example 4) in 1:2 dichloromethane/acetone (v/v) at 25° C., (2) slurry with Form X (Example 5) in 1:1 dichloromethane/acetone (v/v), or slurry with From X2 (Example 6). (See also FIG. 1.)

Figure 2:
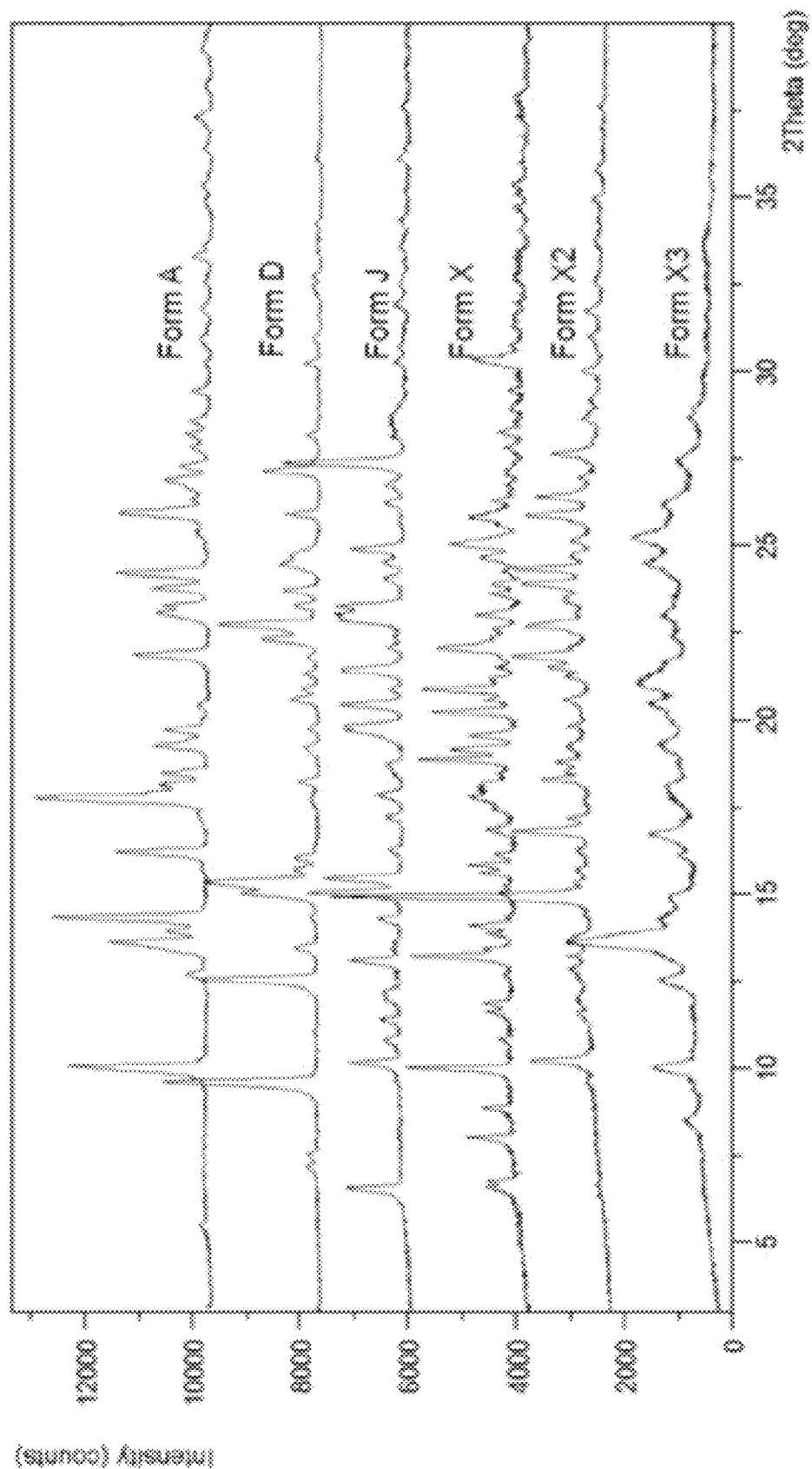
FIG. 2 shows the overlays of X-ray powder diffraction (XRPD) patterns for the polymorphic Forms A, D, J, X, X2, and X3 of grapiprant. Peak intensity is plotted as a function of degrees 2-theta.

FIG. 2 presents the characteristic X-ray powder diffraction pattern for Form A. Form A exhibited diffraction peaks above background at 5.326, 9.978, 12.599, 13.542, 13.803, 14.263, 16.121, 17.665, 18.053, 18.389, 19.126, 19.603, 20.314, 21.781, 22.949, 23.178, 23.663, 24.136, 25.803, 26.792, 27.160, 27.703, 28.125, 28.466, 29.326, 30.813, 31.699, 32.501, 33.219, 35.217, 36.285, 37.180, 38.079, and 39.141 degrees 2-theta. This crystalline form had predominant peaks at about 9.9, about 13.5, about 14.3, about 16.1, about 17.7, about 21.8, about 24.14, and about 25.8 degrees 2-theta (±0.15 degrees 2-theta).

Figure 3:
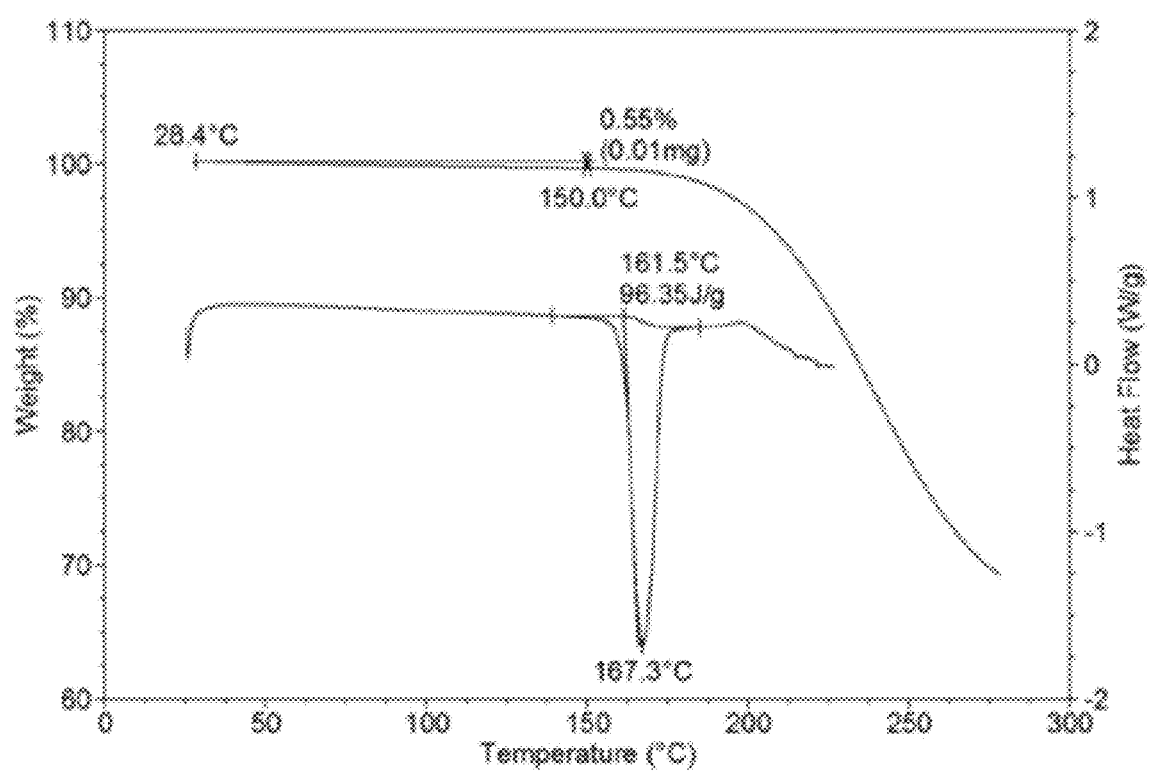
FIG. 3 shows the thermal gravimetric analysis (TGA) and differential scanning calorimetry (DSC) data for Form A of grapiprant.

FIG. 3 presents DSC traces of Form A showed an endotherm/exotherm at about 155-170° C. In the same figure, TGA traces exhibited a loss of mass of 0.5-0.6% when heated from about 30° to about 150° C. The loss of mass was identified as residual acetone and dichloromethane.

Figure 9:
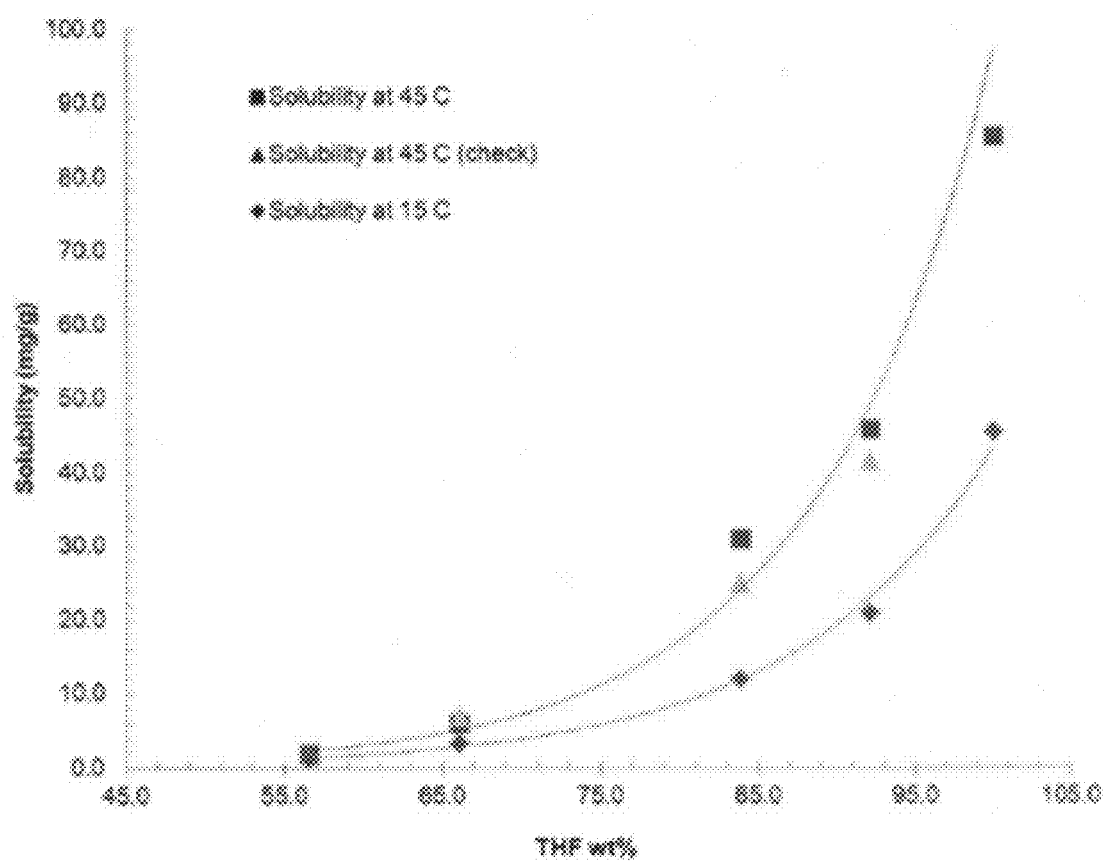
FIG. 9 shows the solubility profile for Form A in a solvent system of tetrahydrofuran (THF) and n-heptane.
Figure 10:
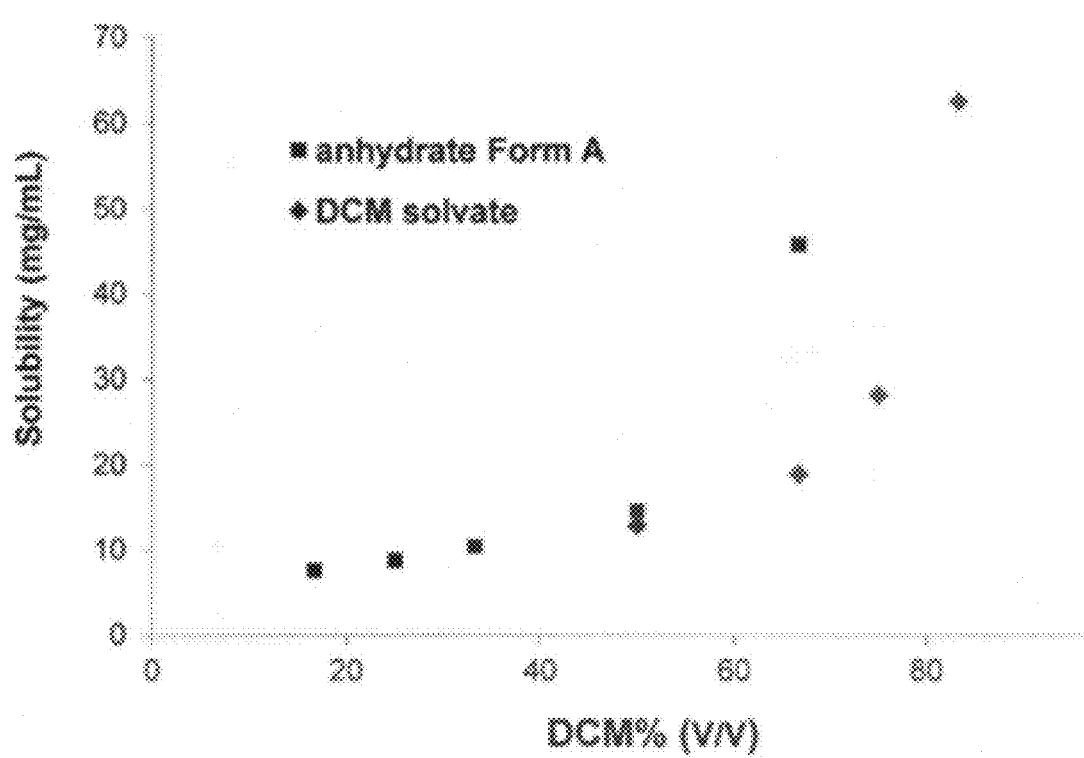
FIG. 10 shows the solubility of profile for Form A in a solvent system of dichloromethane (DCM) and acetone.

FIG. 9 shows the solubility profile for Form A in a solvent system of tetrahydrofuran (THF) and n-heptane, and FIG. 10 shows the solubility of profile for Form A in a solvent system of dichloromethane and acetone. These solubilities were evaluated to indicate how recrystallization solvents perform in the overall recovery of materials.

Example 3

Preparation and Characterization of Form D Crystals

Form D of grapiprant is a dihydrate, having about 6.5 by weight of water. Form D crystals were prepared by slurry of Form A (Example 2) in water. (See also FIG. 1.)

FIG. 2 presents the characteristic X-ray powder diffraction pattern for Form D. Form D exhibited diffraction peaks above background at 7.179, 7.511, 9.642, 12.493, 12.598, 13.411, 14.318, 14.978, 15.402, 15.694, 16.053, 17.680, 18.202, 19.223, 19.746, 20.570, 20.888, 21.327, 21.792, 22.313, 22.766, 23.284, 23.284, 23.676, 24.450, 24.755, 25.902, 27.142, 28.159, 30.224, 30.904, 32.374, 32.725, 34.237, 34.237, and 36.142 degrees 2-theta. This crystalline form had predominant peaks at about 9.6, about 12.5, about 15.0, about 15.4, about 22.7, and about 27.1 degrees 2-theta (±0.15 degrees 2-theta).

Figure 4:
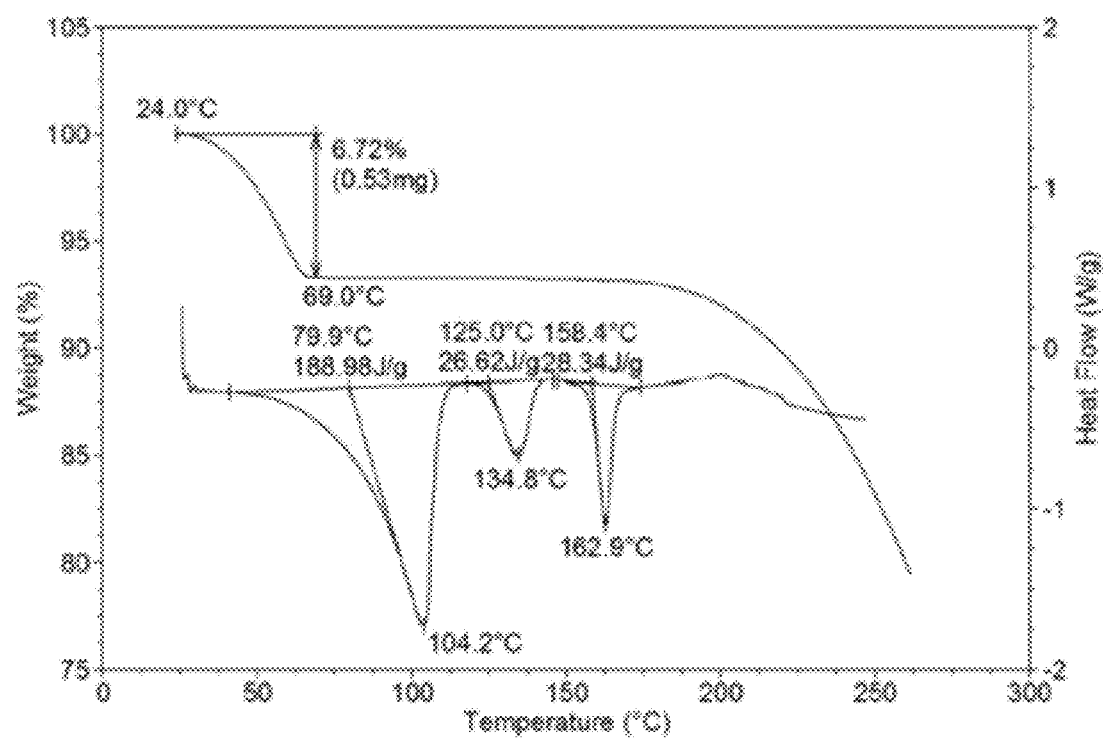
FIG. 4 shows TGA and DSC data for Form D of grapiprant.

FIG. 4 presents DSC traces of Form D showed endotherm/exotherm events at about 25-125° C., at about 125-155° C., and at about 155-175° C. In the same figure, TGA traces exhibited a loss of mass of 6-7% when heated from about 24° to about 69° C. The loss of mass was identified as water.

Example 4

Preparation and Characterization of Form J Crystals

Figure 23:
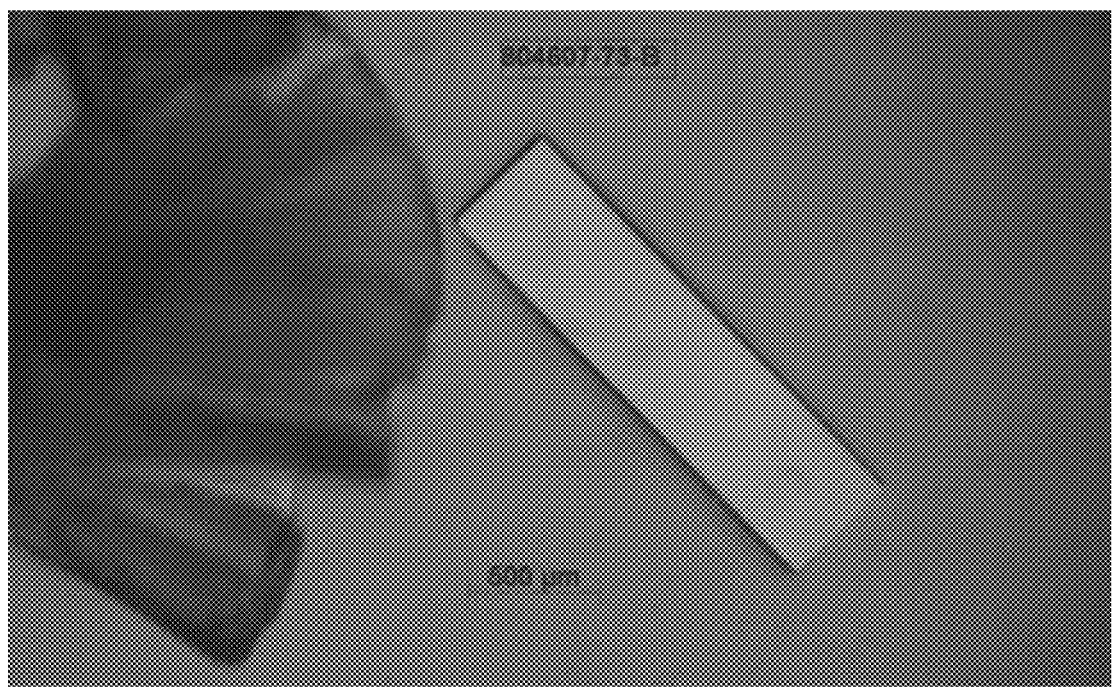
FIG. 23 is a photomicrograph depicting polymorph Form J as a plate crystal. The scale bar is 500 μm, indicating that the crystal is about 500 μm wide and about 1900 μm long.

Form J of grapiprant is a dichloromethane (DCM) solvate, having an unidentified amount of water. Form J crystals were prepared by precipitating grapiprant in 2:1 dichloromethane/n-heptane (2:1). (See also FIG. 1.) As depicted at FIG. 23, Form J may have the crystal morphology of a plate.

FIG. 2 presents the characteristic X-ray powder diffraction pattern for Form J. Form J exhibited diffraction peaks above background at 6.601, 10.158, 10.847, 11.432, 13.119, 14.281, 15.039, 15.470, 16.287, 17.810, 19.661, 20.479, 20.864, 21.395, 22.098, 22.857, 23.295, 24.767, 26.292, 27.343, 28.280, and 36.158 degrees 2-theta. This crystalline form had predominant peaks at about 6.6, about 13.1, about 15.5, about 19.7, and about 22.9 degrees 2-theta (±0.15 degrees 2-theta).

Figure 5:
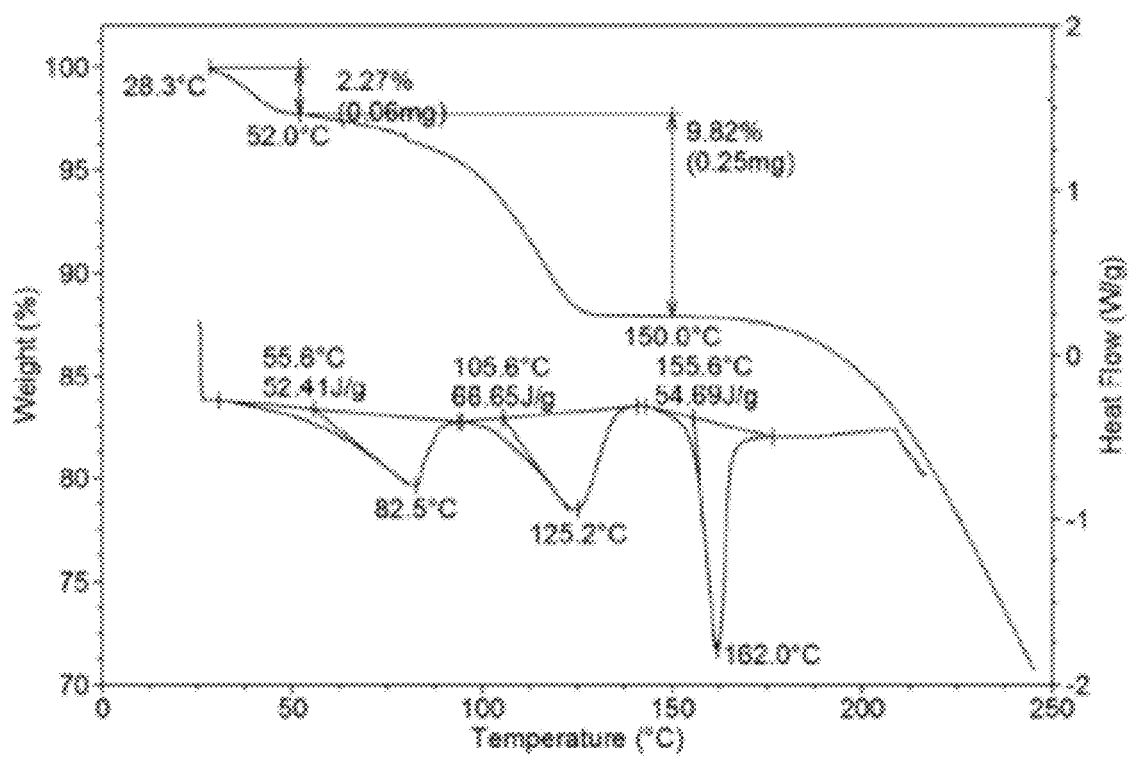
FIG. 5 shows TGA and DSC data for Form J of grapiprant.

FIG. 5 presents DSC traces of Form J showed endotherm/exotherm events at about 25-105° C., at about 105-140° C., and at about 140-190° C. In the same figure, TGA traces exhibited a loss of mass of 10-11% when heated from about 28° to about 150° C. The loss of mass was identified as dichloromethane.

Example 5

Preparation and Characterization of Form X Crystals

Form X of grapiprant is a DCM solvate/hydrate, having an unidentified amount of water. Form X crystals were prepared by slurry of Forms D and J in 2:1 dichloromethane/acetone (v/v). (See also FIG. 1.)

FIG. 2 presents the characteristic X-ray powder diffraction pattern for Form X. Form X exhibited diffraction peaks above background at 6.472, 10.062, 10.700, 11.282, 11.892, 12.097, 12.982, 13.285, 14.181, 14.926, 15.335, 16.164, 17.108, 17.730, 18.615, 19.577, 19.711, 20.315, 20.769, 21.313, 21.941, 22.712, 22.880, 23.142, 23.934, 24.359, 24.785, 26.121, 26.662, 27.261, 27.998, 28.622, 30.176, 31.793, 34.211, 35.970, and 37.491 degrees 2-theta. This crystalline form had predominant peaks at about 6.5, about 10.1, about 14.9, about 15.3, about 19.7, about 20.3, about 21.3, about 22.7, about 23.1, and about 27.3 degrees 2-theta (±0.15 degrees 2-theta).

Figure 6:
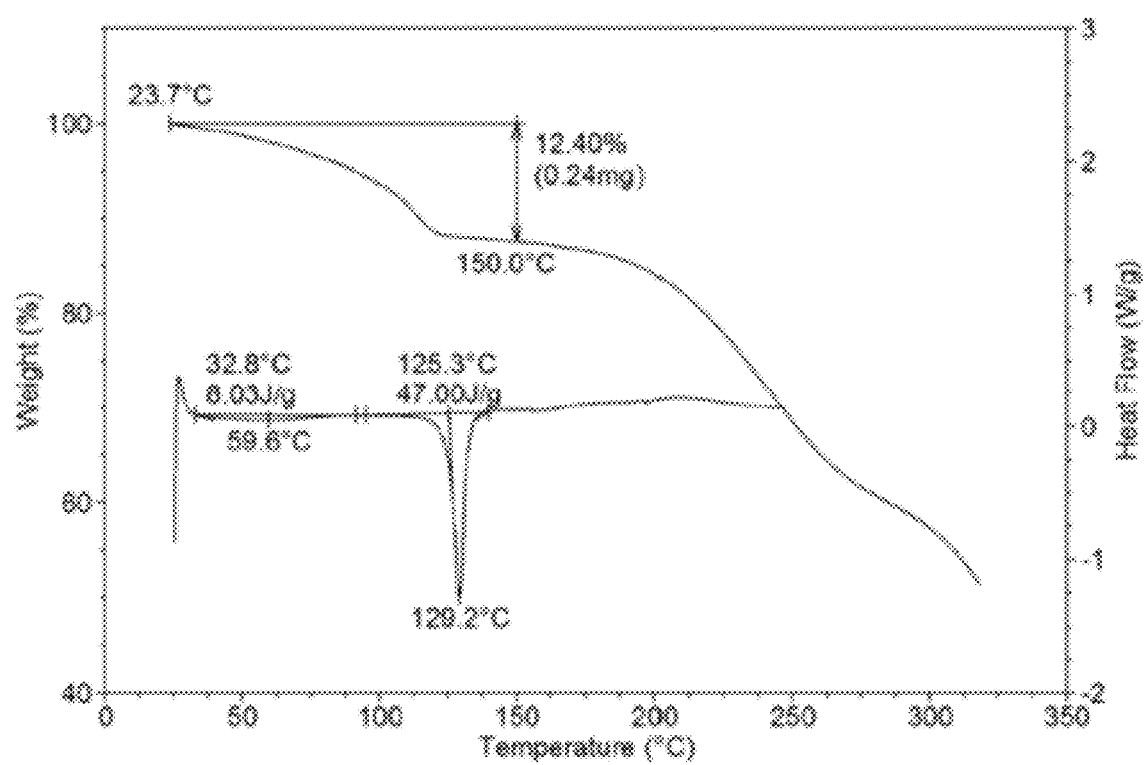
FIG. 6 shows TGA and DSC data for Form X of grapiprant.

FIG. 6 presents DSC traces of Form X showed endotherm/exotherm events at about 33-80° C. and at about 110-140° C. In the same figure, TGA traces exhibited a loss of mass of 12-13% when heated from about 24° to about 150° C. The loss of mass was identified as dichloromethane and water.

Example 6

Preparation and Characterization of Form X2 Crystals

Form X2 of grapiprant is a DCM solvate/hydrate, having between about 0% and about 3.5% by weight of water. Form X2 crystals were prepared by slurry of Form A in 33:66:1 dichloromethane/acetone/water (v/v/v). (See also FIG. 1.)

FIG. 2 presents the characteristic X-ray powder diffraction pattern for Form X2. Form X2 exhibited diffraction peaks above background at 10.227, 12.020, 12.855, 13.221, 13.703, 14.919, 15.667, 16.234, 16.809, 17.170, 18.283, 18.791, 19.259, 19.815, 20.587, 21.227, 21.489, 21.812, 22.659, 23.445, 23.884, 24.338, 24.743, 25.131, 25.883, 26.391, 26.946, 27.629, 28.621, 29.995, 30.964, 31.757, 32.607, 33.716, 34.920, and 35.788 degrees 2-theta. This crystalline form had predominant peaks at about 10.2, about 14.9, about 16.8, about 18.3, about 21.8, about 22.7, about 23.9, about 24.3 about 25.9, and about 26.4 degrees 2-theta (±0.15 degrees 2-theta).

Figure 7:
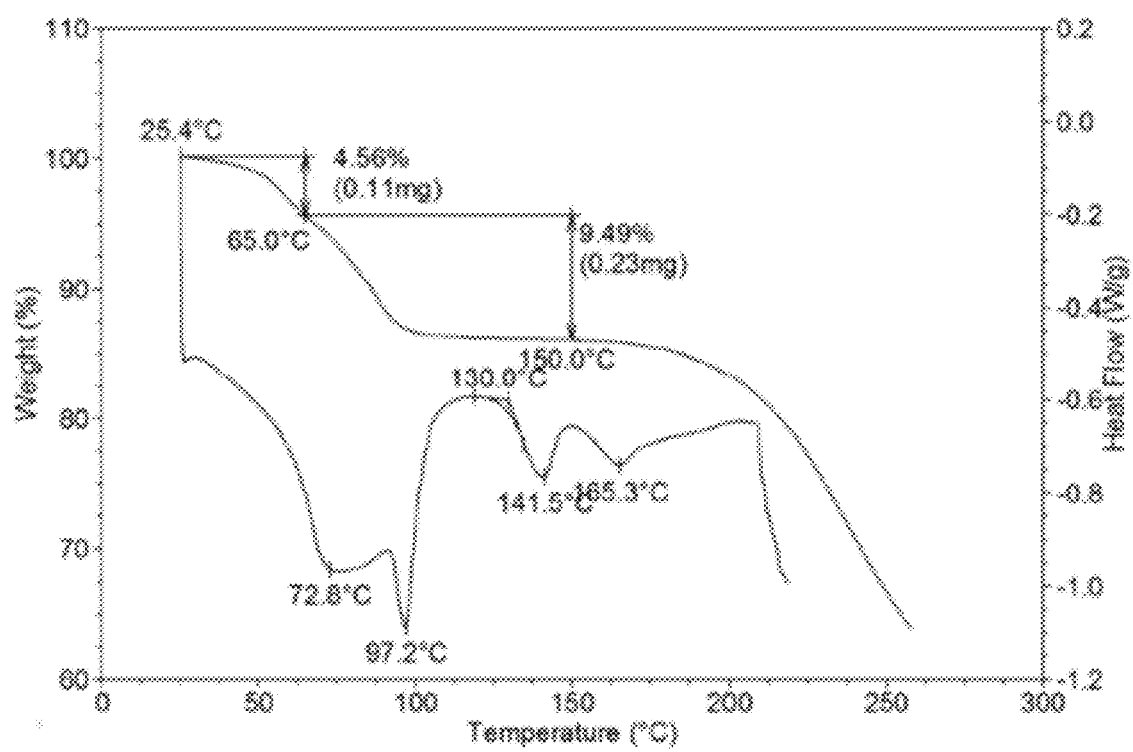
FIG. 7 shows TGA and DSC data for Form X2 of grapiprant.

FIG. 7 presents DSC traces of Form X2 showed endotherm/exotherm events at about 25-130° C., at about 130-150° C., and at about 150-190° C. In the same figure, TGA traces exhibited a loss of mass of 14-15% when heated from about 25° to about 150° C. The loss of mass was identified as dichloromethane and water. (See also FIG. 1.)

Example 7

Preparation and Characterization of Form X3 Crystals

Form X3 of grapiprant is a solvate/hydrate, having between about 1.1% and about 2.4% by weight of water. Form X3 crystals were prepared by drying Form X2 (Example 6) at room temperature or 45° C. (See also FIG. 1.)

FIG. 2 presents the characteristic X-ray powder diffraction pattern for Form X3. Form X3 exhibited diffraction peaks above background at 8.498, 10.042, 12.468, 13.609, 14.303, 14.923, 16.086, 16.773, 18.086, 19.231, 20.463, 21.010, 22.995, 24.477, 25.257, 26.206, 27.448, 28.739, and 33.619 degrees 2-theta. This crystalline form had predominant peaks at about 13.6, about 21.0, about 24.5, and about 25.3 degrees 2-theta (±0.15 degrees 2-theta).

Figure 8:
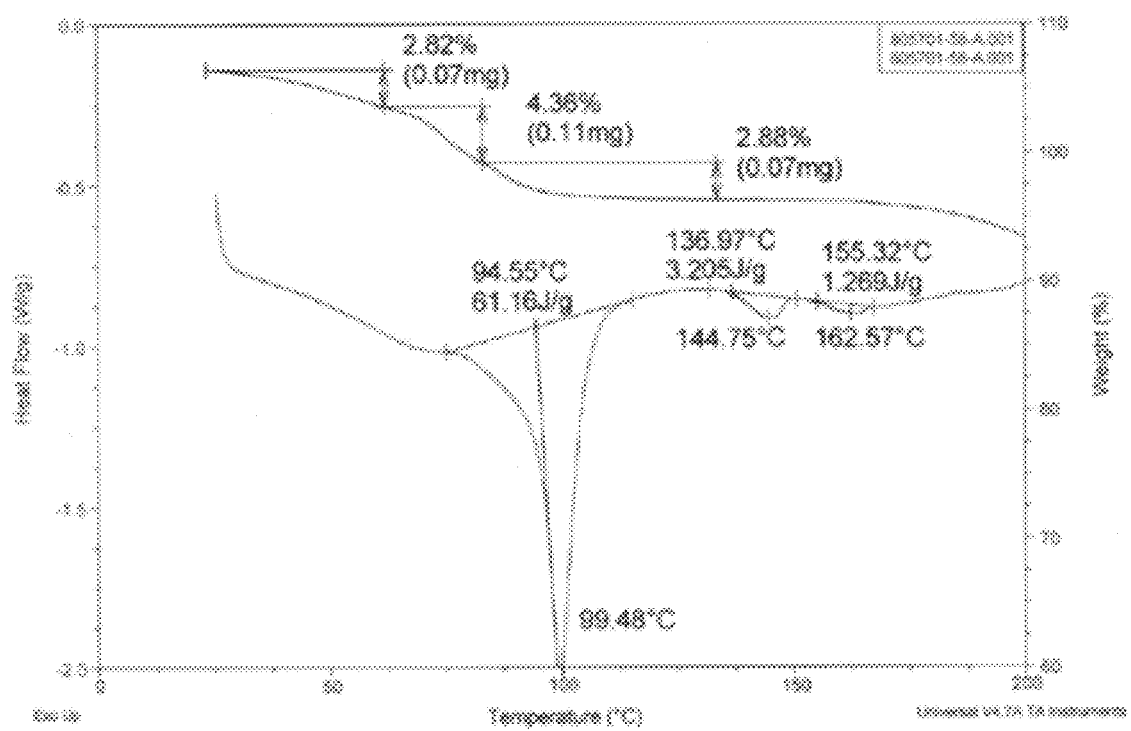
FIG. 8 shows TGA and DSC data for Form X3 of grapiprant.

FIG. 8 presents DSC traces of Form X3 showed endotherm/exotherm events at about 75-115° C., at about 135-150° C., and at about 150-170° C. In the same figure, TGA traces exhibited a loss of mass of 10-11% when heated from about 25° to about 135° C. The loss of mass was identified as water.

Example 8

Preparation and Characterization of Form F Crystals

Form F of grapiprant is a metastable chloroform desolvate, having an unidentified amount of water. Form F crystals were prepared by crystallization of grapiprant from a slurry in 2:3 dichloromethane/chloroform (v/v) at room temperature, from 1:1 acteone/chloroform (v/v), or from 5:1 chloroform/acetone (v/v).

Figure 13:
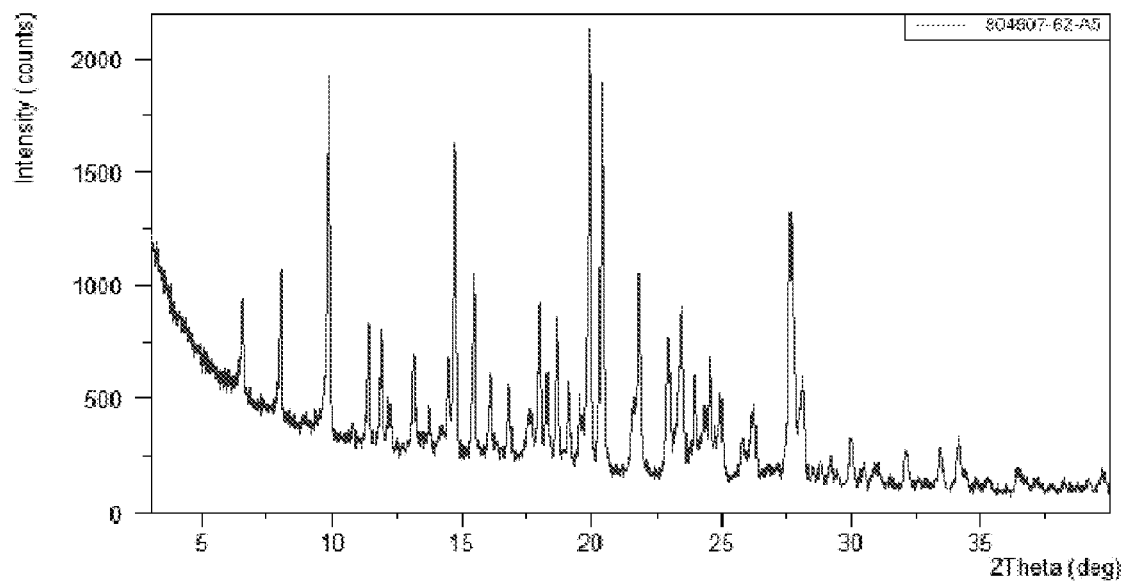
FIG. 13 shows the XRPD pattern for the polymorphic Form F of grapiprant. Peak intensity is plotted as a function of degrees 2-theta.

FIG. 13 presents the characteristic X-ray powder diffraction pattern for Form F. Form F exhibited diffraction peaks above background at 6.564, 8.047, 9.888, 11.430, 11.931, 13.152, 14.483, 14.759, 15.498, 16.129, 16.829, 17.669, 18.003, 18.288, 18.674, 19.111, 19.570, 19.924, 20.409, 21.835, 22.974, 23.485, 23.970, 24.564, 25.002, 26.284, 27.668, 28.158, and 34.174 (relative peak intensity >10%) degrees 2-theta. This crystalline form had predominant peaks at about 9.9, about 14.8, about 15.5, about 18.0, about 19.9, about 20.4, about 21.8, about 23.5, and about 27.7 degrees 2-theta (±0.15 degrees 2-theta).

Figure 14:
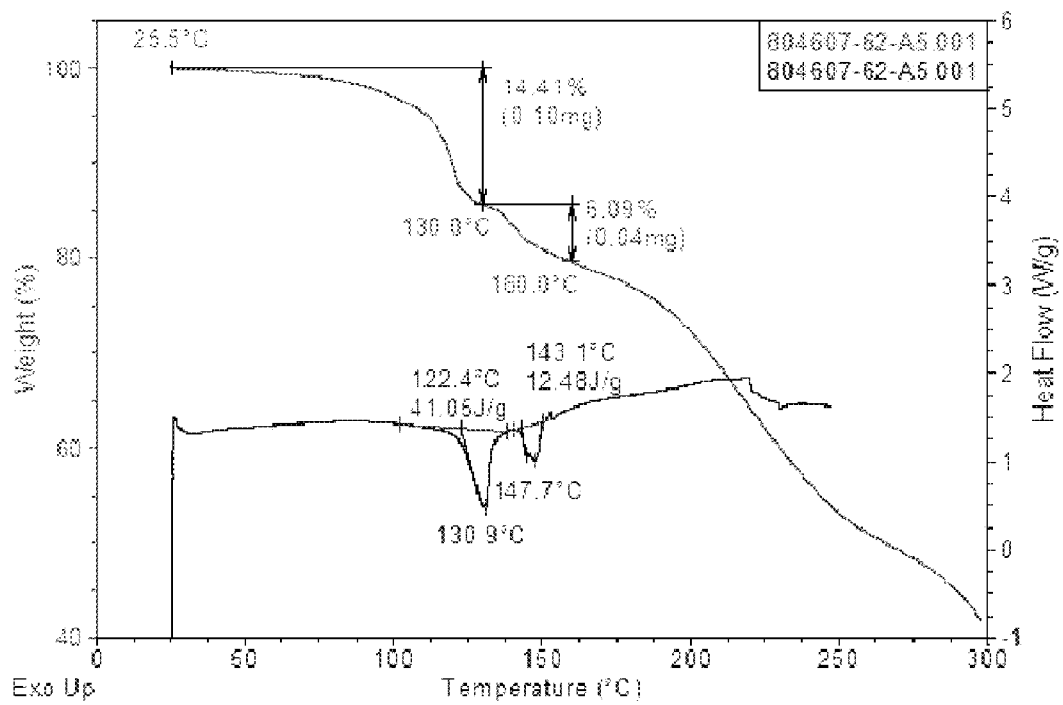
FIG. 14 shows TGA and DSC data for Form F of grapiprant.

FIG. 14 presents DSC traces of Form F showed endotherm/exotherm events at about 122° C. and at about 143° C. In the same figure, TGA traces exhibited a loss of mass of about 20.5% when heated from about 25° to about 135° C. The loss of mass was identified as water.

Example 9

Preparation and Characterization of Form K Crystals

Form K of grapipranth as an unidentified amount of water. Form K crystals were prepared by crystallization of grapiprant from 5:1 dichloromethane/acetonitrile (v/v).

Figure 15:
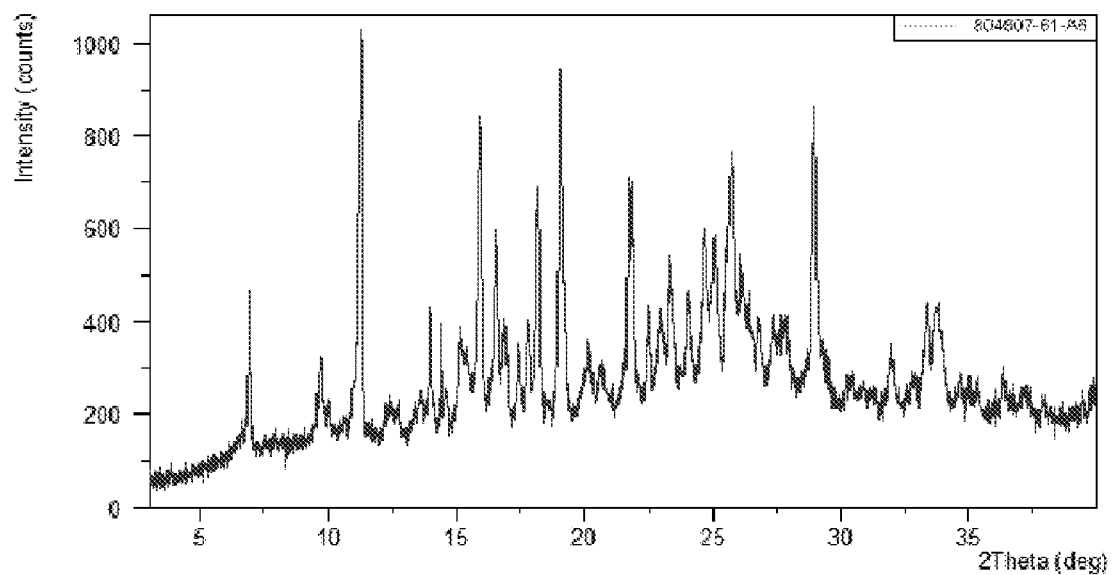
FIG. 15 shows the XRPD pattern for the polymorphic Form K of grapiprant. Peak intensity is plotted as a function of degrees 2-theta.

FIG. 15 presents the characteristic X-ray powder diffraction pattern for Form K. Form K exhibited diffraction peaks above background at 6.914, 9.683, 11.304, 12.380, 13.986, 14.391, 15.133, 15.942, 16.559, 16.870, 17.446, 17.771, 18.189, 19.044, 20.183, 21.714, 21.862, 22.498, 23.309, 24.054, 24.669, 25.083, 26.834, 27.836, 28.964, 31.968, 33.366, and 33.739 (relative peak intensity >10%) degrees 2-theta. This crystalline form had predominant peaks at about 11.3, about 15.9, about 16.6, about 18.2, about 19.0, about 21.7, about 21.9, about 25.7, and about 29.0 degrees 2-theta (±0.15 degrees 2-theta).

Figure 16:
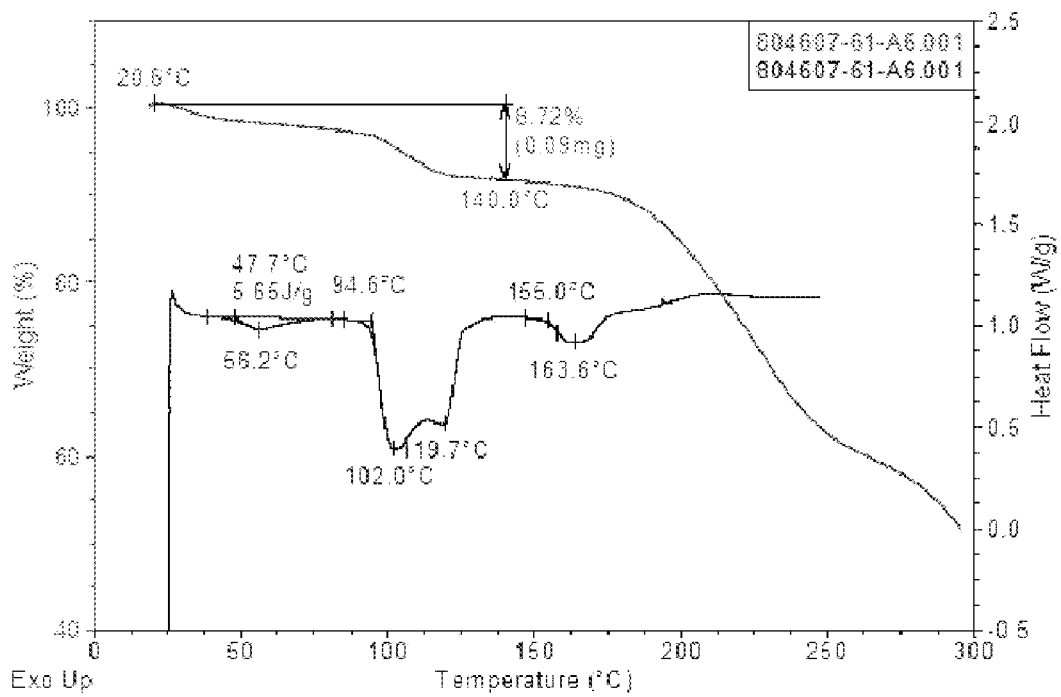
FIG. 16 shows TGA and DSC data for Form K of grapiprant.

FIG. 16 presents DSC traces of Form K showed endotherm/exotherm events at about 48° C., at about 95° C., and at about 155° C. In the same figure, TGA traces exhibited a loss of mass of about 8.7% when heated from about 25° to about 135° C. The loss of mass was identified as water.

Example 10

Preparation and Characterization of Form L Crystals

Form L of grapiprant has an unidentified amount of water. Form L crystals were prepared by crystallization of grapiprant from dichloromethane/acetonitrile or from dichloromethane/ethanol.

Figure 17:
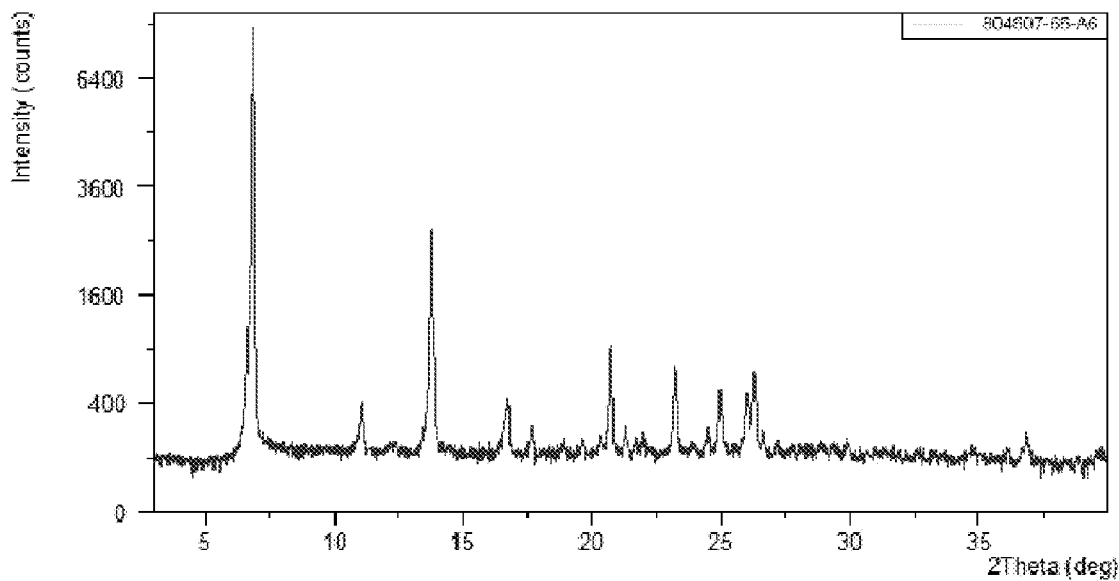
FIG. 17 shows the XRPD pattern for the polymorphic Form L of grapiprant. Peak intensity is plotted as a function of degrees 2-theta.

FIG. 17 presents the characteristic X-ray powder diffraction pattern for Form L. Form L exhibited diffraction peaks above background at 6.836, 11.066, 13.755, 16.720, 17.636, 20.315, 20.726, 21.305, 21.970, 23.216, 24.491, 24.969, 26.022, 26.282, and 36.864 (relative peak intensity >1%) degrees 2-theta. This crystalline form had predominant peaks at about 6.8, about 11.1, about 13.8, about 16.7, about 20.7, about 23.2, about 25.0, about 26.0, and about 26.3 degrees 2-theta (±0.15 degrees 2-theta).

Figure 18:
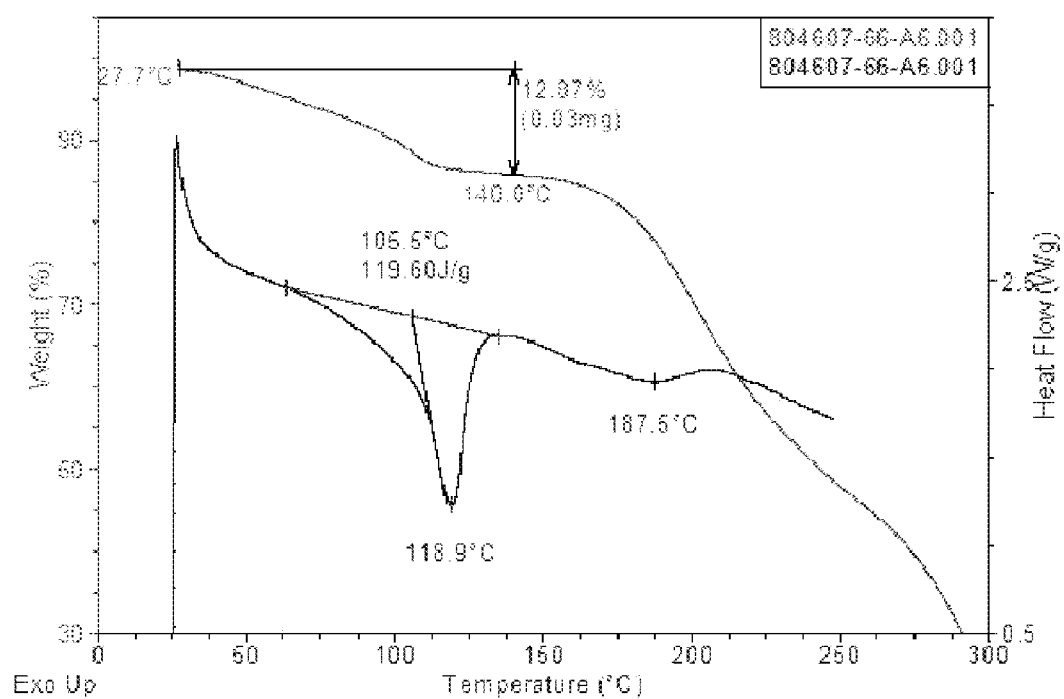
FIG. 18 shows TGA and DSC data for Form L of grapiprant.

FIG. 18 presents DSC traces of Form L showed endotherm/exotherm events at about 106° C. In the same figure, TGA traces exhibited a loss of mass of about 12.9% when heated from about 25° to about 135° C. The loss of mass was identified as water.

Example 11

Preparation and Characterization of Form M Crystals

Form M of grapiprant has an unidentified amount of water. Form M crystals were prepared by crystallization of grapiprant from 7:3 dichloromethane/acetone (v/v).

Figure 19:
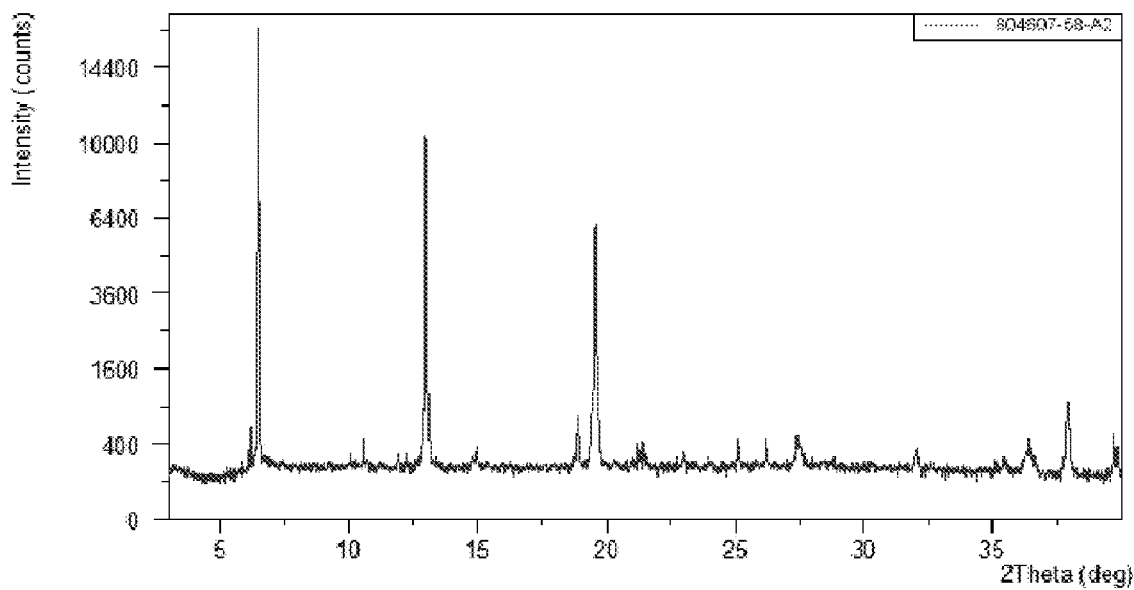
FIG. 19 shows the XRPD pattern for the polymorphic Form M of grapiprant. Peak intensity is plotted as a function of degrees 2-theta.

FIG. 19 presents the characteristic X-ray powder diffraction pattern for Form M. Form M exhibited diffraction peaks above background at 6.162, 6.458, 10.561, 12.981, 14.974, 18.874, 19.538, 21.380, 25.101, 26.176, 27.382, 36.386, 37.883, 37.994, 39.714, and 39.816 (relative peak intensity >1%) degrees 2-theta. This crystalline form had predominant peaks at about 6.2, about 6.5, about 13.0, about 18.9, about 19.5, about 27.4, about 37.9, about 38.0, and about 39.7 degrees 2-theta (±0.15 degrees 2-theta).

Figure 20:
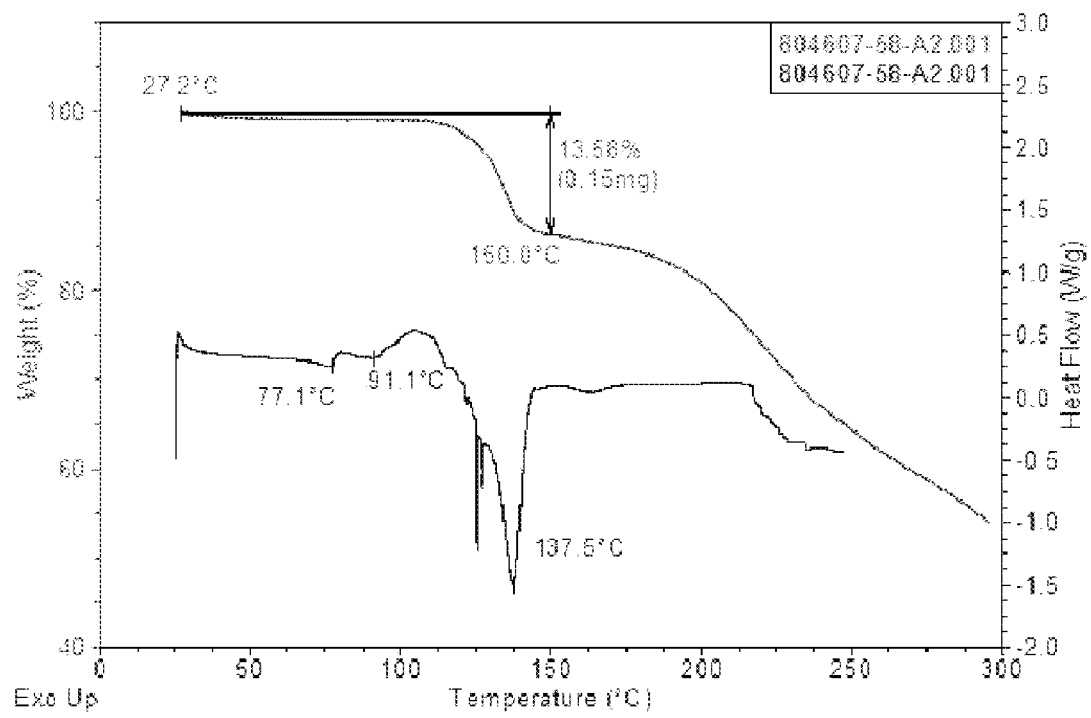
FIG. 20 shows TGA and DSC data for Form M of grapiprant.

FIG. 20 presents DSC traces of Form M showed endotherm/exotherm events at about 77° C., at about 99° C., and at about 138° C. In the same figure, TGA traces exhibited a loss of mass of about 13.6% when heated from about 25° to about 135° C. The loss of mass was identified as water.

Example 12

Preparation and Characterization of Form N Crystals

Form N of grapiprant has an unidentified amount of water. Form N crystals were prepared by crystallization of grapiprant from 5:1 DCM/THF (v/v).

Figure 21:
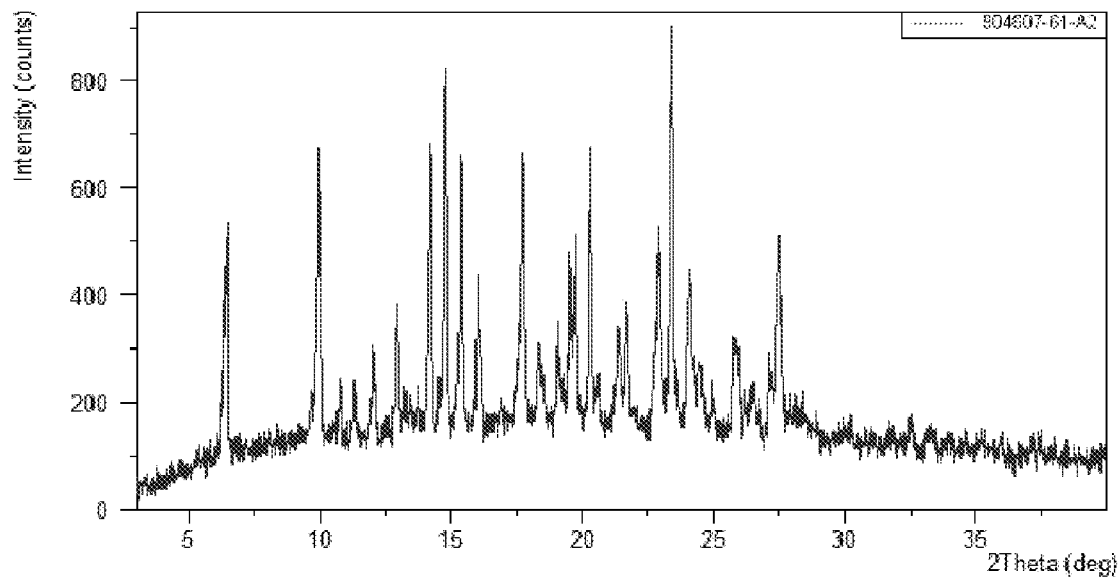
FIG. 21 shows the XRPD pattern for the polymorphic Form N of grapiprant. Peak intensity is plotted as a function of degrees 2-theta.

FIG. 21 presents the characteristic X-ray powder diffraction pattern for Form N. Form N exhibited diffraction peaks above background at 6.357, 6.472, 9.943, 10.007, 10.760, 11.313, 12.016, 12.938, 14.182, 14.763, 15.353, 16.000, 17.737, 18.350, 19.067, 19.506, 19.737, 20.311, 20.590, 21.376, 21.688, 22.912, 23.368, 24.066, 24.476, 25.838, 27.165, and 27.508 (relative peak intensity >10%) degrees 2-theta. This crystalline form had predominant peaks at about 6.5, about 9.9, about 14.2, about 14.8, about 15.4, about 17.7, about 19.7, about 20.3, and about 23.4 degrees 2-theta (±0.15 degrees 2-theta).

Figure 22:
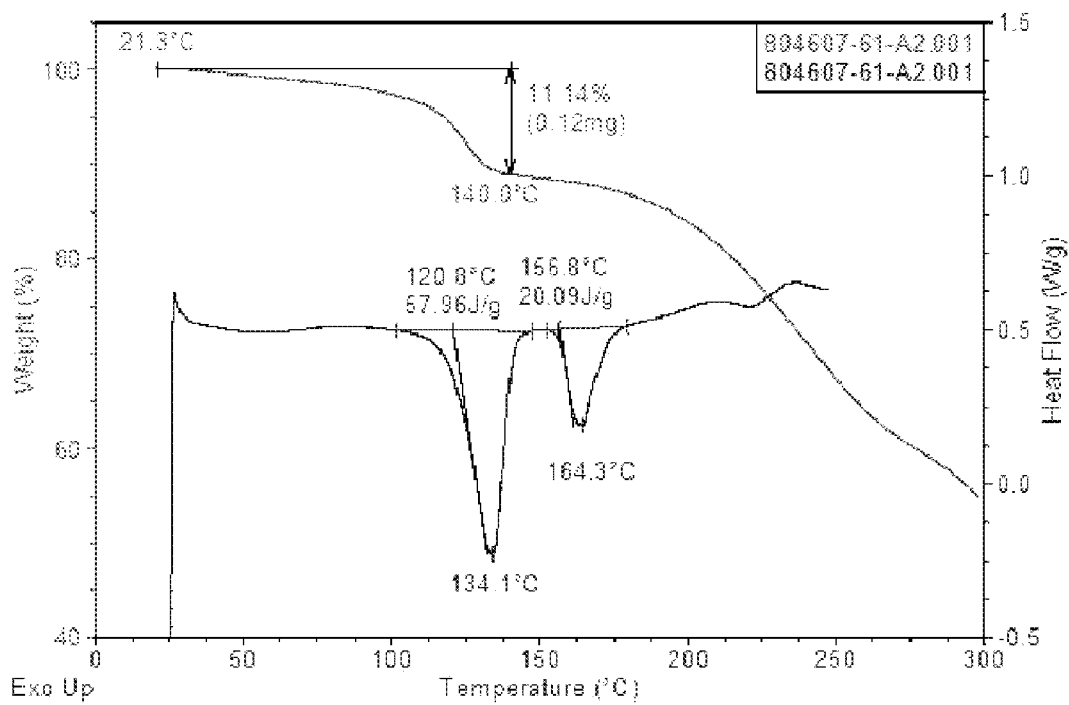
FIG. 22 shows TGA and DSC data for Form N of grapiprant.

FIG. 22 presents DSC traces of Form N showed endotherm/exotherm events at about 121° C. and at about 157° C. In the same figure, TGA traces exhibited a loss of mass of about 11.1% when heated from about 25° to about 135° C. The loss of mass was identified as water.

What is claimed is:

1. A crystalline form of grapiprant selected from the group consisting of Form X, Form X2, Form X3, Form F, Form K, Form L, Form M, and Form N, wherein the crystalline form is selected from the following group:
   i. Form X, which exhibits an X-ray powder diffraction pattern having characteristic peaks expressed in degrees 2-theta at about 6.5, about 10.1, about 14.9, about 15.3, about 19.7, about 20.3, about 21.3, about 22.7, about 23.1, and about 27.3;
   ii. Form X, which exhibits a differential scanning calorimetry profile having endotherm/exotherm events at about 33-80° C. and at about 110-140° C.;
   iii. Form X, which exhibits a thermogravimetric analysis showing a loss of mass of 12-13% when heated from about 24° to about 150° C.;
   iv. Form X2, which exhibits an X-ray powder diffraction pattern having characteristic peaks expressed in degrees 2-theta at about 10.2, about 14.9, about 16.8, about 18.3, about 21.8, about 22.7, about 23.9, about 24.3 about 25.9, and about 26.4;
   v. Form X2, which exhibits a differential scanning calorimetry profile having endotherm/exotherm events at about 25-130° C., at about 130-150° C., and at about 150-190° C.;
   vi. Form X2, which exhibits a thermogravimetric analysis showing a loss of mass of 14-15% when heated from about 25° to about 150° C.;
   vii. Form X3, which exhibits an X-ray powder diffraction pattern having characteristic peaks expressed in degrees 2-theta at about 13.6, about 21.0, about 24.5, and about 25.3;
   viii. Form X3, which exhibits a differential scanning calorimetry profile having endotherm/exotherm events at about 75-115° C., at about 135-150° C., and at about 150-170° C.;
   ix. Form X3, which exhibits a thermogravimetric analysis showing a loss of mass of 10-11% when heated from about 25° to about 135° C.;
   x. Form F, which exhibits an X-ray powder diffraction pattern having characteristic peaks expressed in degrees 2-theta at about 9.9, about 14.8, about 15.5, about 18.0, about 19.9, about 20.4, about 21.8, about 23.5, and about 27.7;
   xi. Form F, which exhibits a differential scanning calorimetry profile having endotherm/exotherm events at about 122° C. and at about 143° C.;
   xii. Form F, which exhibits a thermogravimetric analysis showing a loss of mass of about 20.5% when heated from about 25° to about 135° C.;
   xiii. Form K, which exhibits an X-ray powder diffraction pattern having characteristic peaks expressed in degrees 2-theta at about 11.3, about 15.9, about 16.6, about 18.2, about 19.0, about 21.7, about 21.9, about 25.7, and about 29.0;
   xiv. Form K, which exhibits a differential scanning calorimetry profile having endotherm/exotherm events at about 48° C., about 95° C., and at about 155° C.;
   xv. Form K, which exhibits a thermogravimetric analysis showing a loss of mass of about 8.7% when heated from about 25° to about 135° C.;
   xvi. Form L, which exhibits an X-ray powder diffraction pattern having characteristic peaks expressed in degrees 2-theta at about 6.8, about 11.1, about 13.8, about 16.7, about 20.7, about 23.2, about 25.0, about 26.0, and about 26.3;
   xvii. Form L, which exhibits a differential scanning calorimetry profile having endotherm/exotherm events at about 106° C.;
   xviii. Form L, which exhibits a thermogravimetric analysis showing a loss of mass of about 12.9% when heated from about 25° to about 135° C.;
   xix. Form M, which exhibits an X-ray powder diffraction pattern having characteristic peaks expressed in degrees 2-theta at about 6.2, about 6.5, about 13.0, about 18.9, about 19.5, about 27.4, about 37.9, about 38.0, and about 39.7;
   xx. Form M, which exhibits a differential scanning calorimetry profile having endotherm/exotherm events at about 77° C., at about 99° C., and at about 138° C.;
   xxi. Form M, which exhibits a thermogravimetric analysis showing a loss of mass of about 13.6% when heated from about 25° to about 135° C.;
   xxii. Form N, which exhibits an X-ray powder diffraction pattern having characteristic peaks expressed in degrees 2-theta at about 6.5, about 9.9, about 14.2, about 14.8, about 15.4, about 17.7, about 19.7, about 20.3, and about 23.4;
   xxiii. Form N, which exhibits a differential scanning calorimetry profile having endotherm/exotherm events at about 121° C. and at about 157° C.; and
   xxiv. Form N, which exhibits a thermogravimetric analysis showing a loss of mass of about 11% when heated from about 25° to about 135° C.

2. A pharmaceutical composition, the composition comprising at least one crystalline form of grapiprant of claim 1 and at least one pharmaceutically acceptable excipient, wherein the crystalline form of grapiprant is selected from the group consisting of Form X, Form X2, Form X3, Form F, Form K, Form L, Form M, and Form N, wherein the crystalline form is selected from the following group:
   i. Form X, which exhibits an X-ray powder diffraction pattern having characteristic peaks expressed in degrees 2-theta at about 6.5, about 10.1, about 14.9, about 15.3, about 19.7, about 20.3, about 21.3, about 22.7, about 23.1, and about 27.3;

ii. Form X, which exhibits a differential scanning calorimetry profile having endotherm/exotherm events at about 33-80° C. and at about 110-140° C.;
iii. Form X, which exhibits a thermogravimetric analysis showing a loss of mass of 12-13% when heated from about 24° to about 150° C.;
iv. Form X2, which exhibits an X-ray powder diffraction pattern having characteristic peaks expressed in degrees 2-theta at about 10.2, about 14.9, about 16.8, about 18.3, about 21.8, about 22.7, about 23.9, about 24.3 about 25.9, and about 26.4;
v. Form X2, which exhibits a differential scanning calorimetry profile having endotherm/exotherm events at about 25-130° C., at about 130-150° C., and at about 150-190° C.;
vi. Form X2, which exhibits a thermogravimetric analysis showing a loss of mass of 14-15% when heated from about 25° to about 150° C.;
vii. Form X3, which exhibits an X-ray powder diffraction pattern having characteristic peaks expressed in degrees 2-theta at about 13.6, about 21.0, about 24.5, and about 25.3;
viii. Form X3, which exhibits a differential scanning calorimetry profile having endotherm/exotherm events at about 75-115° C., at about 135-150° C., and at about 150-170° C.;
ix. Form X3, which exhibits a thermogravimetric analysis showing a loss of mass of 10-11% when heated from about 25° to about 135° C.;
x. Form F, which exhibits an X-ray powder diffraction pattern having characteristic peaks expressed in degrees 2-theta at about 9.9, about 14.8, about 15.5, about 18.0, about 19.9, about 20.4, about 21.8, about 23.5, and about 27.7;
xi. Form F, which exhibits a differential scanning calorimetry profile having endotherm/exotherm events at about 122° C. and at about 143° C.;
xii. Form F, which exhibits a thermogravimetric analysis showing a loss of mass of about 20.5% when heated from about 25° to about 135° C.;
xiii. Form K, which exhibits an X-ray powder diffraction pattern having characteristic peaks expressed in degrees 2-theta at about 11.3, about 15.9, about 16.6, about 18.2, about 19.0, about 21.7, about 21.9, about 25.7, and about 29.0;
xiv. Form K, which exhibits a differential scanning calorimetry profile having endotherm/exotherm events at about 48° C., about 95° C., and at about 155° C.;
xv. Form K, which exhibits a thermogravimetric analysis showing a loss of mass of about 8.7% when heated from about 25° to about 135° C.;
xvi. Form L, which exhibits an X-ray powder diffraction pattern having characteristic peaks expressed in degrees 2-theta at about 6.8, about 11.1, about 13.8, about 16.7, about 20.7, about 23.2, about 25.0, about 26.0, and about 26.3;
xvii. Form L, which exhibits a differential scanning calorimetry profile having endotherm/exotherm events at about 106° C.;
xviii. Form L, which exhibits a thermogravimetric analysis showing a loss of mass of about 12.9% when heated from about 25° to about 135° C.;
xix. Form M, which exhibits an X-ray powder diffraction pattern having characteristic peaks expressed in degrees 2-theta at about 6.2, about 6.5, about 13.0, about 18.9, about 19.5, about 27.4, about 37.9, about 38.0, and about 39.7;
xx. Form M, which exhibits a differential scanning calorimetry profile having endotherm/exotherm events at about 77° C., at about 99° C., and at about 138° C.;
xxi. Form M, which exhibits a thermogravimetric analysis showing a loss of mass of about 13.6% when heated from about 25° to about 135° C.;
xxii. Form N, which exhibits an X-ray powder diffraction pattern having characteristic peaks expressed in degrees 2-theta at about 6.5, about 9.9, about 14.2, about 14.8, about 15.4, about 17.7, about 19.7, about 20.3, and about 23.4;
xxiii. Form N, which exhibits a differential scanning calorimetry profile having endotherm/exotherm events at about 121° C. and at about 157° C.; and
xxiv. Form N, which exhibits a thermogravimetric analysis showing a loss of mass of about 11% when heated from about 25° to about 135° C.

3. A process for preparing a substantially pure crystalline Form A of grapiprant, the process comprising:
  i. contacting grapiprant at ambient temperature with a solvent comprising dichloromethane and acetone to form a saturated or a near saturated solution; and
  ii. forming crystals of the substantially pure crystalline Form A of grapiprant,
  wherein the crystalline Form A exhibits an X-ray powder diffraction pattern having characteristic peaks expressed in degrees 2-theta at about 9.9, about 13.5, about 14.3, about 16.1, about 17.7, about 21.8, about 24.14, and about 25.8;
  a differential scanning calorimetry profile having showed an endotherm/exotherm at about 155-170° C.; and
  a thermogravimetric analysis showing a loss of mass of 0.5-0.6% when heated from about 30° to about 150° C.

4. The process of claim 3, wherein the solvent comprises a volume-to-volume ratio from 1:1 to 1:3 of dichloromethane/acetone.

5. The process of claim 4, wherein the solvent comprises 0 wt. % to 0.5 wt. % water.

6. A process for preparing a substantially pure crystalline Form X of grapiprant, the process comprising:
  i. contacting grapiprant at 35° C. with a solvent comprising dichloromethane/acetone in a 1:0.5 to 1:5 volume-to-volume ratio to form a suspension; and
  ii. forming crystals of the substantially pure crystalline Form X of grapiprant,
    wherein the crystalline Form X, which exhibits an X-ray powder diffraction pattern having characteristic peaks expressed in degrees 2-theta at about 6.5, about 10.1, about 14.9, about 15.3, about 19.7, about 20.3, about 21.3, about 22.7, about 23.1, and about 27.3;
    a differential scanning calorimetry profile having endotherm/exotherm events at about 33-80° C. and at about 110-140° C.; and
    a thermogravimetric analysis showing a loss of mass of 12-13% when heated from about 24° C. to about 150° C.

7. The process of claim 6, wherein the solvent comprises a volume-to-volume ratio from 1:1 to 2:1.

8. The process of claim 6, further comprising converting Form X to Form A by slurry in dichloromethane/acetone with a volume-to-volume ratio of 1:1,
  wherein Form A exhibits an X-ray powder diffraction pattern having characteristic peaks expressed in degrees 2-theta at about 9.9, about 13.5, about 14.3, about 16.1, about 17.7, about 21.8, about 24.14, and about 25.8;
  a differential scanning calorimetry profile having showed an endotherm/exotherm at about 155-170° C.; and
  a thermogravimetric analysis showing a loss of mass of 0.5-0.6% when heated from about 30° to about 150° C.

* * * * *